US010275572B2

(12) United States Patent
Alderete, Jr. et al.

(10) Patent No.: US 10,275,572 B2
(45) Date of Patent: Apr. 30, 2019

(54) DETECTING BLOCKAGE OF A RESERVOIR CAVITY DURING A SEATING OPERATION OF A FLUID INFUSION DEVICE

(71) Applicant: MEDTRONIC MINIMED, INC., Northridge, CA (US)

(72) Inventors: Juan M. Alderete, Jr., Granada Hills, CA (US); Alexander S. Campbell, Tarzana, CA (US); Steve Chow, Northridge, CA (US); Hsiao-Yu S. Kow, Ladera Ranch, CA (US); Salman Monirabbasi, Playa Vista, CA (US); Dmytro Y. Sokolovskyy, Simi Valley, CA (US); Andrew E. Weaver, Granada Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 1016 days.

(21) Appl. No.: 14/267,696

(22) Filed: May 1, 2014

(65) Prior Publication Data

US 2015/0314068 A1 Nov. 5, 2015

(51) Int. Cl.
*A61M 5/172* (2006.01)
*G06F 19/00* (2018.01)
(Continued)

(52) U.S. Cl.
CPC ..... *G06F 19/3468* (2013.01); *A61M 5/14216* (2013.01); *A61M 5/14244* (2013.01);
(Continued)

(58) Field of Classification Search
CPC .... A61M 5/16831; A61M 2005/16863; A61M 2205/332; A61M 5/14546; A61M 5/1456;
(Continued)

(56) References Cited

U.S. PATENT DOCUMENTS 3,631,847 A 1/1972 Hobbs, II
4,212,738 A 7/1980 Henne
(Continued)

FOREIGN PATENT DOCUMENTS

DE 4329229 3/1995
EP 0319268 11/1988
(Continued)

OTHER PUBLICATIONS

PCT Search Report (PCT/US02/03299), dated Oct. 31, 2001, Medtronic Minimed, Inc.
(Continued)

*Primary Examiner* — Bhisma Mehta
*Assistant Examiner* — William R Frehe
(74) *Attorney, Agent, or Firm* — Lorenz & Kopf, LLP

(57) ABSTRACT

A fluid infusion device and related operating methods are presented here. An exemplary embodiment of the device includes a drive motor assembly, a force sensor associated with the drive motor assembly, and a reservoir cavity that accommodates fluid reservoirs. An exemplary operating method for the device obtains force measurements for a reservoir seating action of the drive motor assembly, where the force measurements indicate measures of force imparted to the force sensor during the reservoir seating action. The method continues by determining that a vent in the reservoir cavity is blocked, based on an analysis of the force measurements, and by initiating corrective action for the fluid infusion device in response to determining that the vent in the reservoir cavity is blocked.

24 Claims, 13 Drawing Sheets

(51) Int. Cl.
*A61M 5/142* (2006.01)
*G16H 40/63* (2018.01)
*A61M 5/145* (2006.01)

(52) U.S. Cl.
CPC ............ *G06F 19/00* (2013.01); *G16H 40/63* (2018.01); *A61M 5/1452* (2013.01); *A61M 2205/332* (2013.01)

(58) Field of Classification Search
CPC .... A61M 5/14566; A61M 2005/14573; G01L 1/26
See application file for complete search history.

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |

(56) References Cited

U.S. PATENT DOCUMENTS

| | | |
|---|---|---|
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,621,893 B2 | 11/2009 | Moberg et al. |
| 8,197,444 B1 | 6/2012 | Bazargan et al. |
| 8,469,942 B2 | 6/2013 | Kow et al. |
| 8,628,510 B2 | 1/2014 | Bazargan et al. |
| 8,690,855 B2 | 4/2014 | Alderete, Jr. et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2009/0299290 A1* | 12/2009 | Moberg ............... A61M 5/1456 604/151 |
| 2012/0160033 A1* | 6/2012 | Kow .................... G01F 13/00 73/861.71 |

FOREIGN PATENT DOCUMENTS

| | | | |
|---|---|---|---|
| EP | 0806738 | 11/1997 | |
| EP | 0880936 | 12/1998 | |
| EP | 1338295 | 8/2003 | |
| EP | 1631036 A2 | 3/2006 | |
| GB | 2218831 | 11/1989 | |
| JP | 2015198864 A | * 11/2015 | ......... A61B 17/3203 |
| WO | WO 96/20745 | 7/1996 | |
| WO | WO 96/36389 | 11/1996 | |
| WO | WO 96/37246 A1 | 11/1996 | |
| WO | WO 97/21456 | 6/1997 | |
| WO | WO 98/20439 | 5/1998 | |
| WO | WO 98/24358 | 6/1998 | |
| WO | WO 98/42407 | 10/1998 | |
| WO | WO 98/49659 | 11/1998 | |
| WO | WO 98/59487 | 12/1998 | |
| WO | WO 99/08183 | 2/1999 | |
| WO | WO 99/10801 | 3/1999 | |
| WO | WO 99/18532 | 4/1999 | |
| WO | WO 99/22236 | 5/1999 | |
| WO | WO 00/10628 | 3/2000 | |
| WO | WO 00/19887 | 4/2000 | |
| WO | WO 00/48112 | 8/2000 | |
| WO | WO 02/058537 A2 | 8/2002 | |
| WO | WO 03/001329 | 1/2003 | |
| WO | WO 03/094090 | 11/2003 | |
| WO | WO 2005/065538 A2 | 7/2005 | |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting a Primer for Insulin Pump Users to Zero in on Good Control. MiniMed Inc.

(56) References Cited

OTHER PUBLICATIONS

Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMedn™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine -co-n-butyl nethacrylate," Medical Progress Through Technology, vol. 21, 1995, pp. 91-103.

(56) References Cited

OTHER PUBLICATIONS

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Disaccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

DETECTING BLOCKAGE OF A RESERVOIR CAVITY DURING A SEATING OPERATION OF A FLUID INFUSION DEVICE

TECHNICAL FIELD

Embodiments of the subject matter described herein relate generally to medical devices. More particularly, embodiments of the subject matter relate to fluid infusion devices such as personal insulin infusion pumps.

BACKGROUND

Portable medical devices are useful for patients that have conditions that must be monitored on a continuous or frequent basis. For example, diabetics are usually required to modify and monitor their daily lifestyle to keep their blood glucose (BG) in balance. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly.

The prior art includes a number of fluid infusion devices and insulin pump systems that are designed to deliver accurate and measured doses of insulin via infusion sets (an infusion set delivers the insulin through a small diameter tube that terminates at, e.g., a cannula inserted under the patient's skin). In lieu of a syringe, the patient can simply activate the insulin pump to administer an insulin bolus as needed, for example, in response to the patient's high BG level.

A typical infusion pump includes a housing, which encloses a pump drive system, a fluid containment assembly, an electronics system, and a power supply. The pump drive system typically includes a small drive motor or motor assembly (DC, stepper, solenoid, or other varieties) and drive train components such as gears, screws, and levers that convert rotational motor motion to a translational displacement of a stopper or piston of a fluid reservoir. The fluid containment assembly typically includes the fluid reservoir with the actuation piston, tubing, and a catheter or infusion set to create a fluid path for carrying medication from the reservoir to the body of a user. The electronics system regulates power from the power supply to the motor. The electronics system may include programmable controls to operate the motor continuously or at periodic intervals to obtain a closely controlled and accurate delivery of the medication over an extended period.

Some fluid infusion devices use sensors and alarm features designed to detect and indicate certain operating conditions, such as non-delivery of the medication to the patient due to a fluid path occlusion. In this regard, a force sensor can be used in a fluid infusion device to detect the amount of force imparted by the motor assembly and/or an actuator to the piston of the fluid reservoir. The force sensor in such a fluid infusion device could be positioned at the end of the drive motor assembly that actuates a rotatable drive screw, which moves an actuator, which in turn advances the piston of the reservoir. With such an arrangement, the force applied to the force sensor by the drive motor assembly is proportional to the pressure applied to the piston as a result of power supplied to the drive system to advance the piston. Thus, when a certain force threshold (a set point corresponding to an occlusion condition) is reached, the fluid infusion device is triggered to generate an alarm to warn the user.

Some fluid infusion devices use replaceable fluid reservoirs that are secured in the reservoir cavity of the device and actuated by the drive assembly. One form of infusion pump utilizes a removable threaded cap that accommodates replacement and refilling of fluid reservoirs, and that is used to seat and secure the fluid reservoir in the housing of the pump. Assuming that the pump had previously completed a rewind operation, the user unscrews the threaded cap to remove an empty reservoir, refills the reservoir or replaces the old reservoir with a new reservoir, and reinstalls the threaded cap to secure the filled reservoir in place. After installing a reservoir, the pump is operated to perform a seating action during which the actuator is advanced forward until it reaches and seats with the piston of the fluid reservoir. The force sensor may be used during the seating action to detect when proper seating has occurred.

The reservoir cavity is typically sealed to inhibit ingress of fluid and contaminants, such that the fluid reservoir and electronics inside the housing remain protected. Although sealed to inhibit fluid and particulates, the reservoir cavity may include a vent structure or element that allows air to flow into and out of the reservoir cavity. The reservoir cavity vent is desirable to equalize the pressure inside the reservoir cavity, regardless of the position of the reservoir actuator. If this vent is blocked, however, pressure could increase inside the reservoir cavity during seating operations because the forward advance of the actuator reduces the interior volume of the reservoir cavity, which in turn results in increased pressure (due to the unvented and sealed state of the reservoir cavity). Unpredictable buildup of pressure in this manner is undesirable because it can impact the accuracy of the reservoir seating operation, which relies on force measurements as mentioned above.

Accordingly, it is desirable to have an improved reservoir seating technique for fluid infusion devices. In addition, it is desirable to have a methodology for detecting a blocked reservoir cavity vent during a reservoir seating operation. Furthermore, other desirable features and characteristics will become apparent from the subsequent detailed description and the appended claims, taken in conjunction with the accompanying drawings and the foregoing technical field and background.

BRIEF SUMMARY

A method of operating a fluid infusion device is presented here. An exemplary embodiment of the device includes a drive motor assembly, a force sensor associated with the drive motor assembly, and a reservoir cavity that accommodates fluid reservoirs. In accordance with certain exemplary embodiments, the method obtains a plurality of force measurements for a reservoir seating action of the drive motor assembly, the plurality of force measurements indicating measures of force imparted to the force sensor during the reservoir seating action. The method continues by determining that a vent in the reservoir cavity is blocked, based on an analysis of the plurality of force measurements, and by initiating corrective action for the fluid infusion device in response to determining that the vent in the reservoir cavity is blocked.

Also presented here is another exemplary embodiment of a method of operating a fluid infusion device. The device includes a drive motor assembly, an actuator coupled to the drive motor assembly, and a reservoir cavity that accommodates a fluid reservoir having a piston. The method begins by initiating a reservoir seating action intended to seat the actuator with the piston of the fluid reservoir. The method continues by obtaining, for each of a plurality of travel distance measurement points associated with the reservoir seating action, a respective force measurement that is indicative of pressure inside the reservoir cavity. The method continues by processing force measurements for at least two of the plurality of travel distance measurement points, determining that a vent in the reservoir cavity is blocked, based on the processing, and initiating corrective action for the fluid infusion device in response to determining that the vent in the reservoir cavity is blocked.

An exemplary embodiment of a device for delivering fluid to a user is also presented here. The device includes a housing, a reservoir cavity within the housing to accommodate fluid reservoirs, a drive motor assembly in the housing to advance an actuator for a piston of a fluid reservoir, a force sensor associated with the drive motor assembly to generate output levels in response to force imparted thereto, the output levels corresponding to force measurements, and an electronics module coupled to the force sensor to process the output levels during a reservoir seating action intended to seat the actuator with the piston of the fluid reservoir. The electronics module obtains a plurality of plurality of force measurements from the force sensor, determines that a vent in the reservoir cavity is blocked, based on an analysis of the plurality of force measurements, and initiates corrective action for the fluid infusion device in response to determining that the vent in the reservoir cavity is blocked.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

For the sake of brevity, conventional techniques related to infusion system operation, insulin pump and/or infusion set operation, blood glucose sensing and monitoring, force sensors, signal processing, and other functional aspects of the systems (and the individual operating components of the systems) may not be described in detail here. Examples of infusion pumps and/or related pump drive systems used to administer insulin and other medications may be of the type described in, but not limited to, U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; and 7,621,893; which are herein incorporated by reference.

The subject matter described here relates to a fluid infusion device of the type used to treat a medical condition of a patient. The infusion device is used for infusing fluid into the body of a user. The non-limiting examples described below relate to a medical device used to treat diabetes (more specifically, an insulin pump), although embodiments of the disclosed subject matter are not so limited. Accordingly, the infused fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like.

Figure 1:
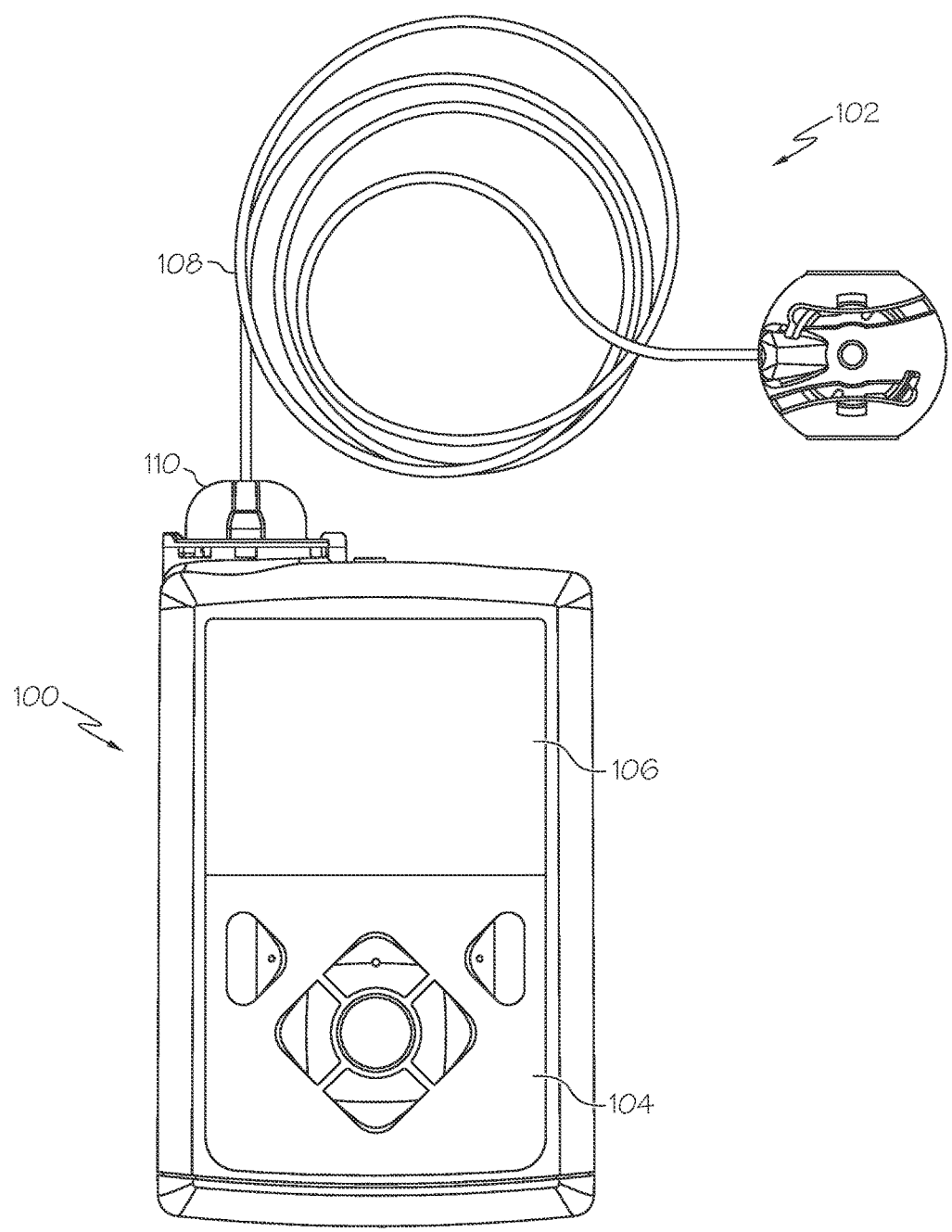
FIG. 1 is a schematic representation of an embodiment of a fluid infusion device.

FIG. 1 is a plan view of an exemplary embodiment of a fluid infusion device 100. FIG. 1 also shows an infusion set 102 coupled to the fluid infusion device 100. The fluid infusion device 100 is designed to be carried or worn by the patient. The fluid infusion device 100 may leverage a number of conventional features, components, elements, and characteristics of existing fluid infusion devices. For example, the fluid infusion device 100 may incorporate some of the features, components, elements, and/or characteristics described in U.S. Pat. Nos. 6,485,465 and 7,621,893, the relevant content of which is incorporated by reference herein.

This embodiment shown in FIG. 1 includes a user interface 104 that includes several buttons that can be activated by the user. These buttons can be used to administer a bolus of insulin, to change therapy settings, to change user preferences, to select display features, and the like. Although not required, the illustrated embodiment of the fluid infusion device 100 includes a display element 106. The display element 106 can be used to present various types of information or data to the user, such as, without limitation: the current glucose level of the patient; the time; a graph or chart of the patient's glucose level versus time; device status indicators; alerts, alarms, error indicators, or other messages; etc. In some embodiments, the display element 106 is realized as a touch screen display element and, therefore, the display element 106 also serves as a user interface component.

The fluid infusion device 100 accommodates a fluid reservoir (hidden from view in FIG. 1) for the fluid to be delivered to the user. A length of tubing 108 is the flow path that couples the fluid reservoir to the infusion set 102. The tubing 108 extends from the fluid infusion device 100 to the infusion set 102, which provides a fluid pathway with the body of the user. A removable cap or fitting 110 is suitably sized and configured to accommodate replacement of fluid reservoirs (which are typically disposable) as needed. In this regard, the fitting 110 is designed to accommodate the fluid path from the fluid reservoir to the tubing 108.

In certain embodiments, the fitting 110 forms a seal with the housing of the fluid infusion device 100, to inhibit ingress of fluid and other potential contaminants into the reservoir cavity. For example, the fitting 110 may include or cooperate with a sealing element that forms the seal when the fitting 110 is threaded onto the housing. Moreover, for the embodiment described here, the fitting 110 includes or cooperates with at least one vent 113 (see FIG. 3) to enable air to pass into and out of the reservoir cavity, thus equalizing the pressure inside the reservoir cavity. In practice, the vent 113 may be implemented as a gas permeable membrane that allows gas (air) to pass while blocking the passage of liquids and solids. In some embodiments, the fluid infusion device 100 may include other venting structures or elements (in lieu of or in addition to a membrane vent) for the reservoir cavity.

Figure 2:
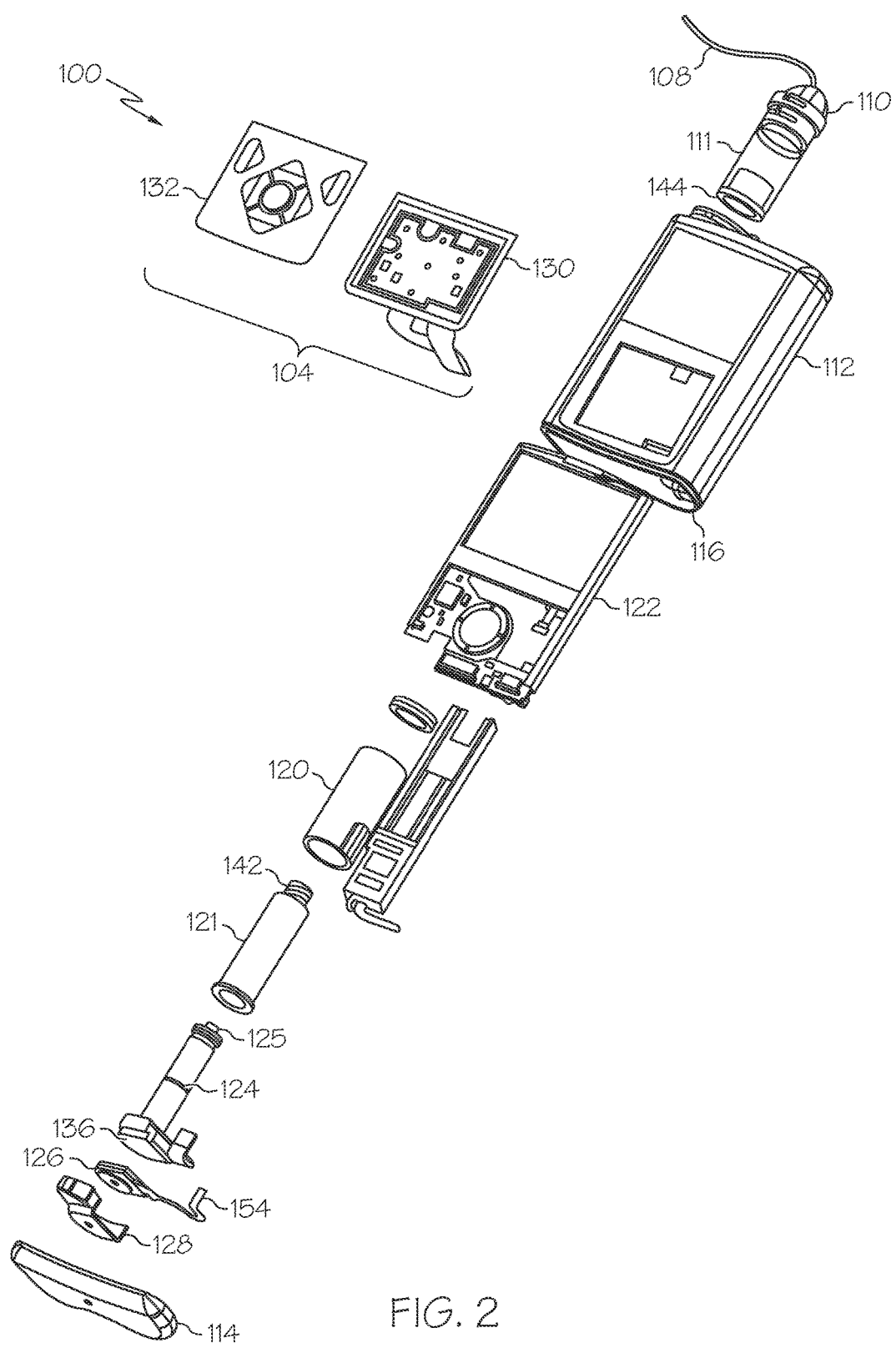
FIG. 2 is an exploded perspective view of the fluid infusion device shown in FIG. 1.

FIG. 2 is an exploded perspective view of the fluid infusion device 100. For the sake of brevity and simplicity, FIG. 2 is a simplified depiction of the fluid infusion device 100 that does not include all of the elements, components, and features that would otherwise be present in a typical embodiment. It should be appreciated that a deployed implementation of the fluid infusion device 100 will include additional features, components, and elements that are not shown in the figures.

The embodiment of the fluid infusion device 100 illustrated in FIG. 2 includes a housing 112 and a housing end cap 114 that is coupled to an end 116 of the housing 112 to enclose components within the housing 112. These internal components include, without limitation: a battery tube subassembly 118; a sleeve 120; a slide actuator 121; an electronics assembly 122; a drive motor assembly 124 having a drive screw 125; a force sensor 126; and a motor support cap 128. FIG. 2 also depicts some components that are located outside the housing 112, namely, a keypad assembly 130 and a graphic keypad overlay 132 for the keypad assembly 130. The keypad assembly 130 and the graphic keypad overlay 132 may be considered to be part of the user interface 104 of the fluid infusion device 100. The outer edge of the motor support cap 128 is attached to the interior side of the housing 112, and the motor support cap 128 contacts the force sensor 126 to remove assembly tolerances from the drive motor assembly 124. FIG. 2 also depicts an exemplary fluid reservoir 111, which is inserted into a reservoir cavity defined within the housing 112. The reservoir cavity is configured, sized, and shaped to accommodate fluid reservoirs, and the fluid reservoir 111 is maintained in the reservoir cavity using the fitting 110. The electronics assembly 122 may include a suitably configured electronics module (not shown in FIG. 2; see FIG. 4 and related description below), which may include or cooperate with a power supply, at least one memory element, at least one processor, processing logic, and device software, firmware, and application programs.

Figure 3:
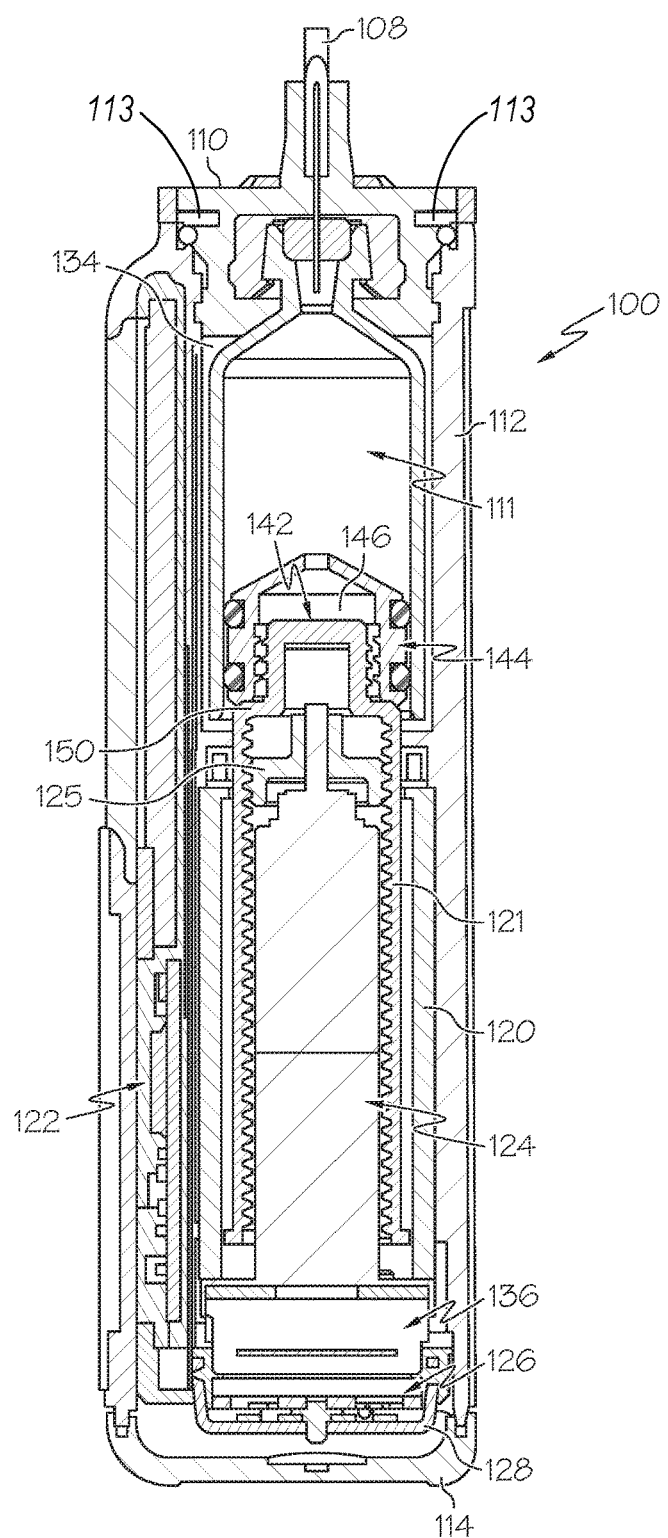
FIG. 3 is a cross sectional view of the fluid infusion device shown in FIG. 1, corresponding to a cross section taken longitudinally through the drive motor assembly and the fluid reservoir.

FIG. 3 is a cross sectional view of the fluid infusion device 100, corresponding to a cross section taken longitudinally through the drive motor assembly 124 and the fluid reservoir 111. FIG. 3 depicts the state of the fluid infusion device 100 after the fluid reservoir 111 has been inserted into the reservoir cavity 134 and after the fitting 110 has been secured to the housing 112 to hold the fluid reservoir 111 in place. While certain embodiments accommodate disposable, prefilled reservoirs, alternative embodiments may use refillable cartridges, syringes or the like. A cartridge can be prefilled with insulin (or other drug or fluid) and inserted into the housing 112. Alternatively, a cartridge could be filled by the user using an appropriate adapter and/or any suitable refilling device.

When assembled as shown in FIG. 3, the drive motor assembly 124 is located in the housing 112. The force sensor 126 is operatively associated with the drive motor assembly 124. For this particular embodiment, the force sensor 126 is coupled to the drive motor assembly 124, and it is located between a base end of the drive motor assembly 124 and the motor support cap 128. In one implementation, the force sensor 126 is affixed to the base end of the drive motor assembly 124 such that the force sensor 126 reacts when it bears against the motor support cap 128. In another implementation, the force sensor 126 is affixed to the housing end cap 114 such that the force sensor 126 reacts when the drive motor assembly 124 bears against the force sensor 126. This configuration and arrangement of the drive motor assembly 124 and the force sensor 126 allows the force sensor 126 to react to forces imparted thereto by the drive motor assembly 124, forces imparted to the drive motor assembly 124 via the fluid pressure of the fluid reservoir 111, and/or forces imparted to the drive motor assembly 124 via air pressure inside the reservoir cavity 134, which can result when the vent 113 is blocked.

The drive motor assembly 124 includes an electric motor 136 that is actuated and controlled by the electronics module of the fluid infusion device 100. The motor 136 is preferably realized as a stepper motor that rotates in a stepwise or discrete manner corresponding to the desired number of fluid delivery strokes. Alternatively, the motor 136 could be a DC motor, a solenoid, or the like. The motor 136 may optionally include an encoder (not shown), which cooperates with the electronics module of the fluid infusion device 100 to monitor the number of motor rotations or portions thereof. This in turn can be used to accurately determine the position of the slide actuator 121, thus providing information relating to the amount of fluid dispensed from the fluid reservoir 111.

The drive motor assembly 124 can be mounted in the housing 112 using an appropriate mounting feature, structure, or element. Alternatively, the mounting could be accomplished using a shaft bearing and leaf spring or other known compliance mountings.

The illustrated embodiment of the drive motor assembly 124 includes a drive member (such as the externally threaded drive gear or drive screw 125) that engages an internally threaded second drive member (such as the slide actuator 121) having a coupler 142. The coupler 142 may be attached to or integrated with the slide actuator 121, as depicted in FIG. 2 and FIG. 3. The slide actuator 121 is sized to fit within the reservoir cavity 134 of the fluid infusion device 100, which enables the slide actuator 121 to operatively cooperate with the fluid reservoir 111. The fluid reservoir 111 includes a plunger or piston 144 with at least one sealing element or feature (e.g., one or more O-rings, integral raised ridges, or a washer) for forming a fluid and air tight seal with the inner wall of the fluid reservoir 111. As mentioned previously, the fluid reservoir 111 is secured into the housing 112 with the fitting 110, which also serves as the interface between the fluid reservoir 111 and the infusion set tubing 108. For this embodiment, the piston 144 is in contact with a linear actuation member, such as the slide actuator 121. For example, the piston 144 may have a female portion 146 that receives the coupler 142 carried by the slide actuator 121. The female portion 146 is positioned at the end face of the piston 144, and it is sized to receive and accommodate the coupler 142. In certain embodiments, the female portion 146 includes a threaded cavity that engages external threads of the coupler 142.

Referring to FIG. 3, rotation of the drive shaft of the motor 136 results in corresponding rotation of the drive screw 125, which in turn moves the slide actuator 121 forward or backward via the threaded engagement. Thus, rotation of the drive screw 125 results in axial displacement of the slide actuator 121 and, therefore, axial displacement of the coupler 142. Such displacement of the coupler 142 moves the piston 144 (upward in FIG. 3) to deliver a predetermined or commanded amount of medication or liquid from the fluid infusion device 100. In this manner, the drive motor assembly 124 is configured to regulate delivery of fluid by actuating the piston 144 (under the control of the electronics module and/or control system of the fluid infusion device 100). As described above, if a stepper motor is employed, then the drive motor assembly 124 can regulate delivery of fluid from the fluid infusion device 100 in discrete actuation or delivery strokes. The fluid infusion device 100 can employ the sleeve 120 or an equivalent feature (such as an anti-rotation key) to inhibit rotation of the drive motor assembly 124, which might otherwise result from torque generated by the motor 136. In some embodiments, the drive shaft of the drive motor assembly 124, the drive screw 125, and the slide actuator 121 are all coaxially centered within the longitudinal axis of travel of the piston 144. In certain alternative embodiments, one or more of these components may be offset from the center of the axis of travel and yet remain aligned with the axis of travel, which extends along the length of the fluid reservoir 111.

As mentioned above, certain embodiments of the fluid infusion device 100 accommodate removable and replaceable fluid reservoirs. When the slide actuator 121 and, therefore, the piston 144 of the fluid reservoir 111 are in their fully extended positions, the piston 144 has forced most, if not all, of the fluid out of the fluid reservoir 111. After the piston 144 has reached the end of its travel path, indicating that the fluid reservoir 111 has been depleted, the fluid reservoir 111 may be removed such that the female portion 146 of the piston 144 disengages from the coupler 142 of the slide actuator 121. After the empty (or otherwise used) fluid reservoir 111 is removed, the electronics module or control system of the fluid infusion device 100 initiates a rewind operation during which the motor 136 rotates in the reverse direction to rewind the slide actuator 121 back to its fully retracted position. Thereafter, a new or refilled fluid reservoir 111 can be installed, seated, and primed for use. In this regard, an embodiment provides for advancement of the slide actuator 121 upon the insertion of a fluid reservoir 111 into the housing 112. The slide actuator 121 advances during a reservoir seating action until its coupler 142 comes into contact with the piston 144 of the fluid reservoir 111. In alternative embodiments having a threaded piston engagement, the slide actuator 121 advances until the threads of the coupler 142 engage the threads in the female portion 146 of the piston 144. When the threads engage in this fashion, they need not do so by twisting. Rather, they may ratchet over one another. In operation, the force sensor 126 may be used to determine when the slide actuator 121 contacts the piston 144, when the coupler 142 is properly seated in the female portion 146, and/or when the fluid reservoir 111 has been primed and is ready to deliver measured doses of fluid.

Although the illustrated embodiment employs a coaxial or inline drive system, alternative configurations could be utilized. For example, a drive system that uses a lead screw, a drive nut, and actuation arms (of the type described in U.S. Pat. No. 6,485,465) may be employed, with the force sensor 126 positioned in an appropriate location. In various embodiments, the drive train might include one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. Moreover, although the illustrated embodiment employs a sensor positioned at the end of the fluid drive train, other arrangements could be deployed. For example, a sensor could be placed at or near the front end of the fluid drive train.

In particular embodiments, the force sensor 126 is used to detect when the slide actuator 121 contacts the piston 144. Thus, after the fluid reservoir 111 is placed into the fluid infusion device 100, the motor 136 is activated to move the slide actuator 121 toward the fluid reservoir 111 to engage the piston 144. In this regard, when a shoulder region 150 (see FIG. 3) of the slide actuator 121 first contacts the piston 144, the electronics module detects an increase in force imparted to the force sensor 126. The measured force continues to increase as the motor 136 continues to drive forward, in response to the fluid resistance in the fluid reservoir 111. When the slide actuator 121 is properly seated with the piston 144, the measured force increases to the seating threshold level. During the seating operation, if the measured force exceeds this seating threshold, the motor 136 is stopped until further commands are issued. The seating threshold is generally about 1.5 pounds. In alternative embodiments, higher or lower seating thresholds may be used depending on the force required to mate the slide actuator 121 with the piston 144, the force required to urge fluid from the fluid reservoir 111, the speed of the motor 136, the accuracy and resolution of the force sensor 126, or the like.

It should be appreciated that other force thresholds can be used for other purposes. During priming of fluid reservoirs, for example, a threshold of about 4.0 pounds is used. In some embodiments, levels greater than about 5.0 pounds are used to detect shock loads that may be damaging to the fluid infusion device 100.

The force sensor 126 is configured to react in response to force imparted thereto. In this regard, electrical, mechanical, magnetic, and/or other measurable or detectable characteristics of the force sensor 126 vary in accordance with the amount of force applied to the force sensor 126. In practice, the force sensor 126 might implement or otherwise leverage known sensor technologies, such as the sensor technology described in U.S. Pat. No. 6,485,465. As shown in FIG. 2, the force sensor 126 includes at least one electrical lead 154 that is electrically coupled to the electronics module (or controller) of the fluid infusion device 100. Alternatively, the force sensor 126 could use wireless data communication technology to provide force-related data to the electronics module. In certain implementations, the force sensor 126 is suitably configured to indicate or generate a plurality of different output levels that can be monitored and/or determined by the electronics module. In practice, the output levels obtained from the force sensor 126 are initially conveyed as analog voltages or analog currents, and the electronics module includes an analog-to-digital converter that transforms a sampled analog voltage into a digital representation. Conversion of sensor voltage into the digital domain is desirable for ease of processing, comparison to threshold values, and the like.

In particular embodiments, the force sensor 126 is realized as an electromechanical component having at least one variable resistance that changes as the force applied to the force sensor 126 changes. In alternative embodiments, the force sensor 126 is a capacitive sensor, a piezoresistive sensor, a piezoelectric sensor, a magnetic sensor, an optical sensor, a potentiometer, a micro-machined sensor, a linear transducer, an encoder, a strain gauge, or the like, and the detectable parameter or characteristic might be compression, shear, tension, displacement, distance, rotation, torque, force, pressure, or the like. In practice, changing characteristics of the force sensor 126 are associated with output signal characteristics that are responsive to a physical parameter to be measured. Moreover, the range and resolution of the monitored output signal provides for the desired number of output levels (e.g., different states, values, quantities, signals, magnitudes, frequencies, steps, or the like) across the range of measurement. For example, the force sensor 126 might generate a low or zero value when the applied force is relatively low, a high or maximum value when the applied force is relatively high, and intermediate values when the applied force is within the detectable range.

In certain exemplary embodiments, the electronics module of the fluid infusion device 100 maintains a constant supply voltage across the force sensor 126, and the monitored output signal of the force sensor 126 is a signal current that passes through a resistive material of the force sensor 126. Thus, the signal current varies with the amount of force applied to the force sensor 126 because the resistance of the force sensor 126 varies with force and the supply voltage across the force sensor 126 is constant. The electronics module converts the monitored signal current into a signal voltage, which is then used as an indication of the force imparted to the force sensor 126 (which may be caused by the drive motor assembly 124, by fluid pressure in the fluid reservoir 111, by impact experienced by the fluid infusion device 100, by unexpected pressure buildup inside the reservoir cavity 134, etc.). In alternative embodiments, a constant supply current is used and the signal voltage across the force sensor 126 varies with force (fluid pressure).

In certain embodiments, sensor measurements are taken prior to commanding the drive system to deliver fluid, and soon after the drive system has stopped delivering fluid. In alternative embodiments, sensor data is collected on a continuous basis at a particular sampling rate (for example, 10.0 Hz, 3.0 Hz, once every 10 seconds, once a minute, once every five minutes, or the like). In further alternative embodiments, the sensor data is only collected prior to commanding the drive system to deliver fluid. In still further alternative embodiments, sensor data is collected during fluid delivery (during delivery strokes and/or between delivery strokes) and during other operations that involve movement of the slide actuator 121.

In practice, the force sensor 126 and associated electronics are designed to measure forces between about zero pounds and about five pounds with a desired resolution of about 0.01 pounds. In preferred embodiments, the force sensor 126 and associated electronics provide a relatively linear voltage output in response to forces applied to the force sensor 126 by one or more drive train components. In alternative embodiments, the range and resolution of the force sensor 126 might vary from that specified above. Furthermore, the sensor range and/or resolution may vary in accordance with the concentration of the fluid being delivered, the diameter of the fluid reservoir 111, the diameter of the fluid path, the nominal range of force experienced during normal operation of the drive motor assembly 124, the amount of sensor noise, the algorithms applied to detect trends from sensor measurements, or the like. Moreover, the fluid infusion device 100 and the force sensor 126 should be suitably configured to survive shock levels that result in much higher forces being applied to the force sensor 126 than the intended sensor measurement range.

Figure 4:
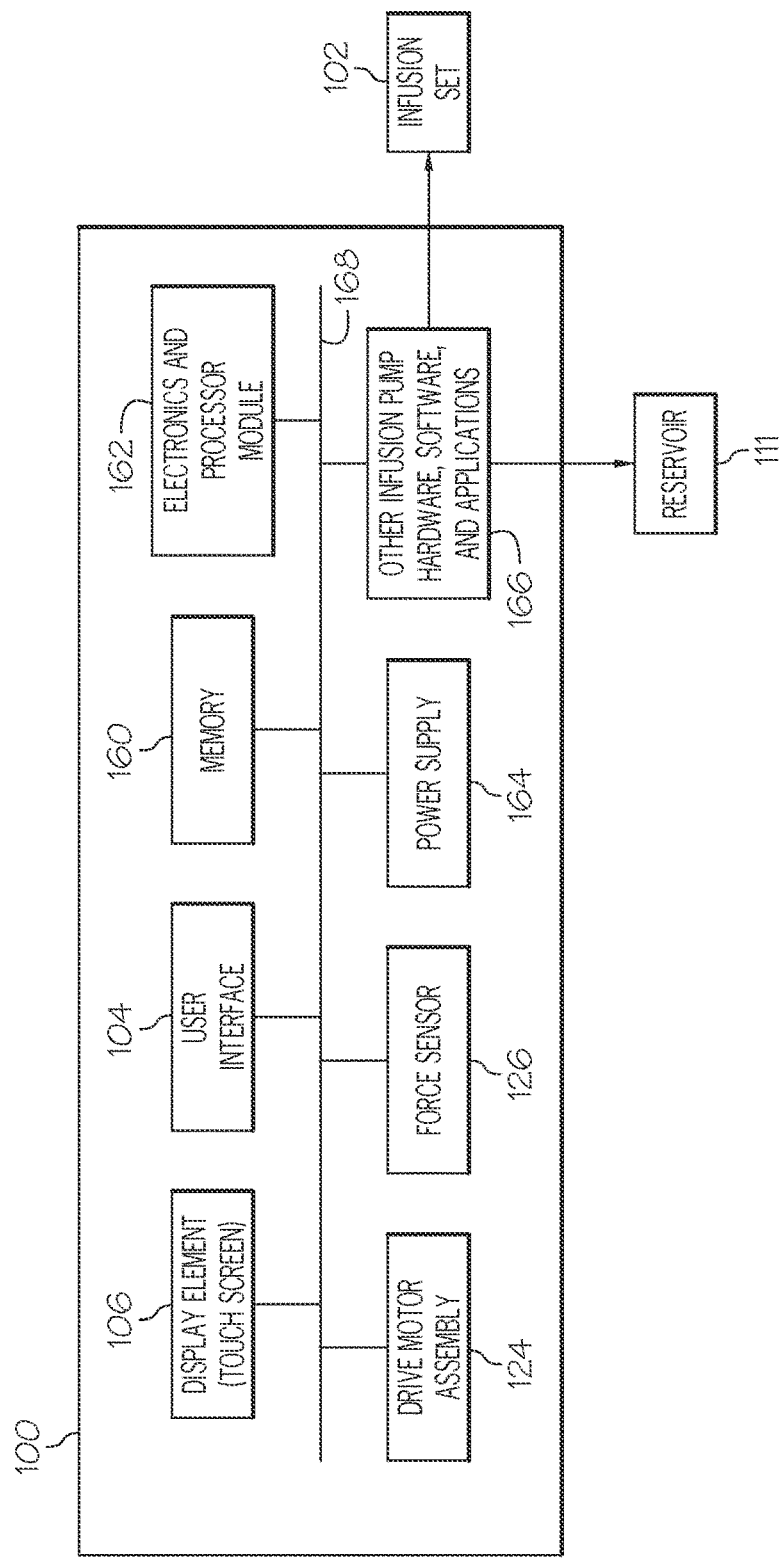
FIG. 4 is a schematic block diagram representation of an embodiment of a fluid infusion device.

As mentioned previously, the fluid infusion device 100 is suitably configured to support a number of techniques, processes, and methodologies that utilize the force sensor 126. In practice, the fluid infusion device 100 includes an electronics module, processing logic, software applications, and/or other features that are used to carry out the various operating processes described here. In this regard, FIG. 4 is a schematic block diagram representation of an embodiment of the fluid infusion device 100. FIG. 4 depicts some previously-described elements of the fluid infusion device 100 as functional blocks or modules, namely, the display element 106; the user interface 104; the drive motor assembly 124; and the force sensor 126. FIG. 4 also depicts the fluid reservoir 111 and the infusion set 102 in block format. This particular embodiment of the fluid infusion device 100 also includes, without limitation: a suitable amount of memory 160; an electronics module 162 (which may include or cooperate with one or more processors, processing modules, controllers, state machines, or the like); a power supply 164 such as a battery or a battery pack; and other infusion pump hardware, software, and applications 166. The elements of the fluid infusion device 100 may be coupled together via an interconnection architecture 168 or arrangement that facilitates transfer of data, commands, power, etc.

The display element 106 represents the primary graphical interface of the fluid infusion device 100. The display element 106 may leverage known plasma, liquid crystal display (LCD), thin film transistor (TFT), and/or other display technologies. The actual size, resolution, and operating specifications of the display element 106 can be selected to suit the needs of the particular application. Notably, the display element 106 may include or be realized as a touch screen display element that can accommodate touch screen techniques and technologies. In practice, the display element 106 may be driven by a suitable display driver to enable the fluid infusion device 100 to display physiological patient data, status information, clock information, alarms, alerts, and/or other information and data received or processed by the fluid infusion device 100.

The user interface 104 may include a variety of items such as, without limitation: a keypad, keys, buttons, a keyboard, switches, knobs (which may be rotary or push/rotary), a touchpad, a microphone suitably adapted to receive voice commands, a joystick, a pointing device, an alphanumeric character entry device or touch element, a trackball, a motion sensor, a lever, a slider bar, a virtual writing tablet, or any device, component, or function that enables the user to select options, input information, or otherwise control the operation of the fluid infusion device 100. In this context, the user interface 104 may cooperate with or include a touch screen display element 106. The user interface 104 allows a user to control the delivery of fluid via the infusion set 102.

The electronics module 162 may include or be implemented with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. A processor device may be realized as a microprocessor, a controller, a microcontroller, or a state machine. Moreover, a processor device may be implemented as a combination of computing devices, e.g., a combination of a digital signal processor and a microprocessor, a plurality of microprocessors, one or more microprocessors in conjunction with a digital signal processor core, or any other such configuration.

The electronics module 162 may include one processor device or a plurality of cooperating processor devices. Moreover, a functional or logical module/component of the fluid infusion device 100 might be realized by, implemented with, and/or controlled by processing logic maintained by or included with the electronics module 162. For example, the display element 106, the user interface 104, the drive motor assembly 124, and/or the infusion pump hardware, software, and applications 166 (or portions thereof) may be implemented in or controlled by the electronics module 162.

The memory 160 may be realized as RAM memory, flash memory, EPROM memory, EEPROM memory, registers, a hard disk, a removable disk, a CD-ROM, or any other form of storage medium known in the art. In this regard, the memory 160 can be coupled to the electronics module 162 such that the electronics module 162 can read information from, and write information to, the memory 160. In the alternative, the memory 160 may be integral to the electronics module 162. As an example, a processor of the electronics module 162 and the memory 160 may reside in an ASIC. In practice, a functional or logical module/component of the fluid infusion device 100 might be realized using program code that is maintained in the memory 160. Moreover, the memory 160 can be used to store data utilized to support the operation of the fluid infusion device 100, including, without limitation, sensor data, force measurements, force thresholds, alert/alarm history, and the like (as will become apparent from the following description).

The infusion pump hardware, software, and applications 166 are utilized to carry out fluid infusion features, operations, and functionality. Thus, the infusion pump hardware, software, and applications 166 may include or cooperate with the infusion set 102 and/or the fluid reservoir 111 (as described above). It should be appreciated that the infusion pump hardware, software, and applications 166 may leverage known techniques to carry out conventional infusion pump functions and operations, and such known aspects will not be described in detail here.

A fluid infusion device can support one or more features or operations that enhance its fluid infusion functionality and/or enhance the user experience of the fluid infusion device. The following sections include descriptions of various processes and methods that may be performed by a fluid infusion device. The various tasks performed in connection with a given process may be performed by software, hardware, firmware, or any combination thereof. For illustrative purposes, a process might be described with reference to elements mentioned above in connection with FIGS. 1-4. In practice, portions of a given process may be performed by different elements of the described system, e.g., a sensor, a drive motor assembly, an electronics module, a processor, or the like. It should be appreciated that a described process may include any number of additional or alternative tasks, the tasks included in a particular flow chart need not be performed in the illustrated order, an embodiment of a described process may omit one or more of the illustrated tasks, and a given process may be incorporated into a more comprehensive procedure or process having additional functionality not described in detail herein.

As mentioned above, the fluid infusion device 100 allows the user to replace a fluid reservoir whenever it becomes depleted. In this regard, a user will manually fill a new reservoir with medication fluid such as insulin, insert the filled reservoir into the reservoir cavity 134 of the fluid infusion device 100 (assuming that a rewind operation has been completed to rewind the slide actuator 121), and perform a seating operation to prepare the reservoir for delivery. During a reservoir seating action, the slide actuator 121 in the reservoir cavity 134 is driven forward until the force sensor 126 detects a force sufficient to indicate that the slide actuator 121 is fully in contact with the reservoir piston 144 (i.e., the "Seating Complete" force). When this happens, the fluid infusion device 100 is ready for fluid delivery.

The fitting 110 (i.e., the reservoir cap) contains a venting mechanism such as the vent 113 that allows air to escape the reservoir cavity 134 through a permeable membrane. If air does not escape as expected, then the "Seating Complete" force may be detected before the slide actuator 121 actually makes contact with the piston 144. This happens because the slide actuator 121 compresses air inside the reservoir cavity 134 while advancing toward the piston 144. In practical embodiments, the permeability of the venting membrane to air decreases if it becomes wet, which may cause air to be trapped in the reservoir cavity 134 instead of venting externally. Moreover, it has been discovered that certain off-label actions (performed by a user during reservoir filling but prior to the insertion of the reservoir into the reservoir cavity 134) may result in seating being initiated with a wet venting membrane.

Figure 5:
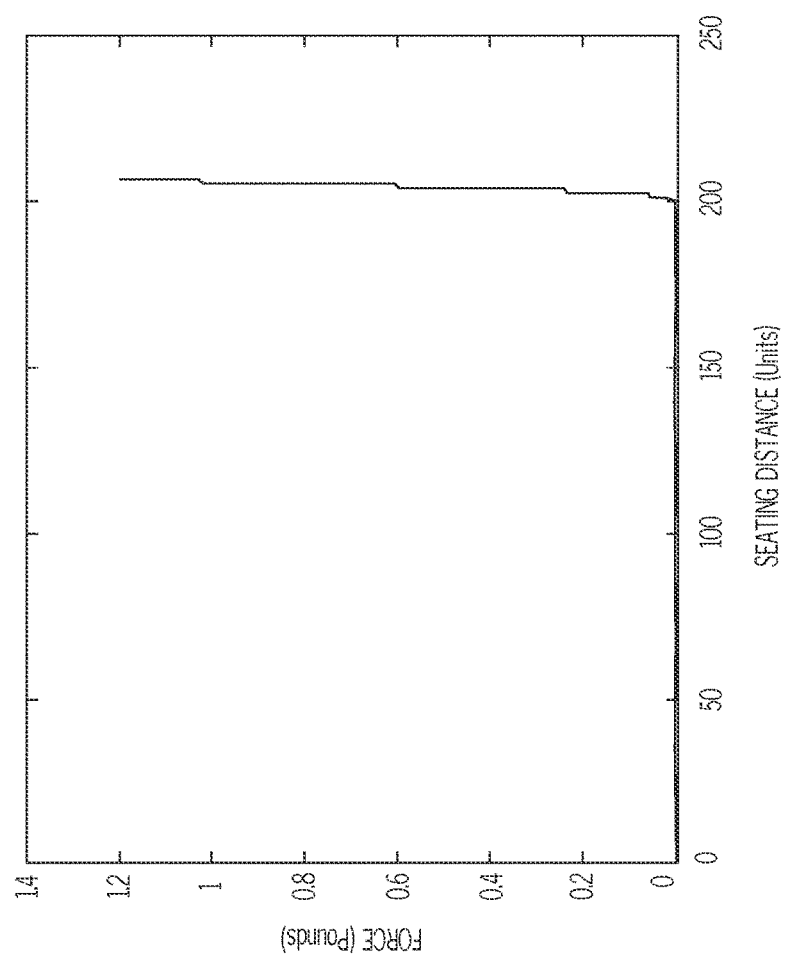
FIG. 5 is a plot of force versus slide actuator position (or an equivalent metric) during a reservoir seating action performed under normal conditions.

In accordance with certain embodiments of the fluid infusion device 100, the control software instructs the motor to drive the slide actuator 121 forward and samples the force sensor output every 0.5 seconds. During a typical seating operation under normal conditions, the force measurement will remain relatively low and stable for the majority of the duration of seating, and will rapidly rise to the threshold force that is associated with proper seating. In this regard, FIG. 5 is a plot of force versus slide actuator position (or drive motor count, travel distance, or any suitable metric) during a reservoir seating action performed under normal conditions. FIG. 5 illustrates how the measured force quickly jumps from its nominal baseline value, which is close to zero pounds, to the seating threshold value of about 1.2 pounds after completion of the seating process. For the illustrated example, the seating process is completed when the slide actuator 121 has traveled a distance that corresponds to the delivery of approximately 200 Units of fluid.

Figure 6:
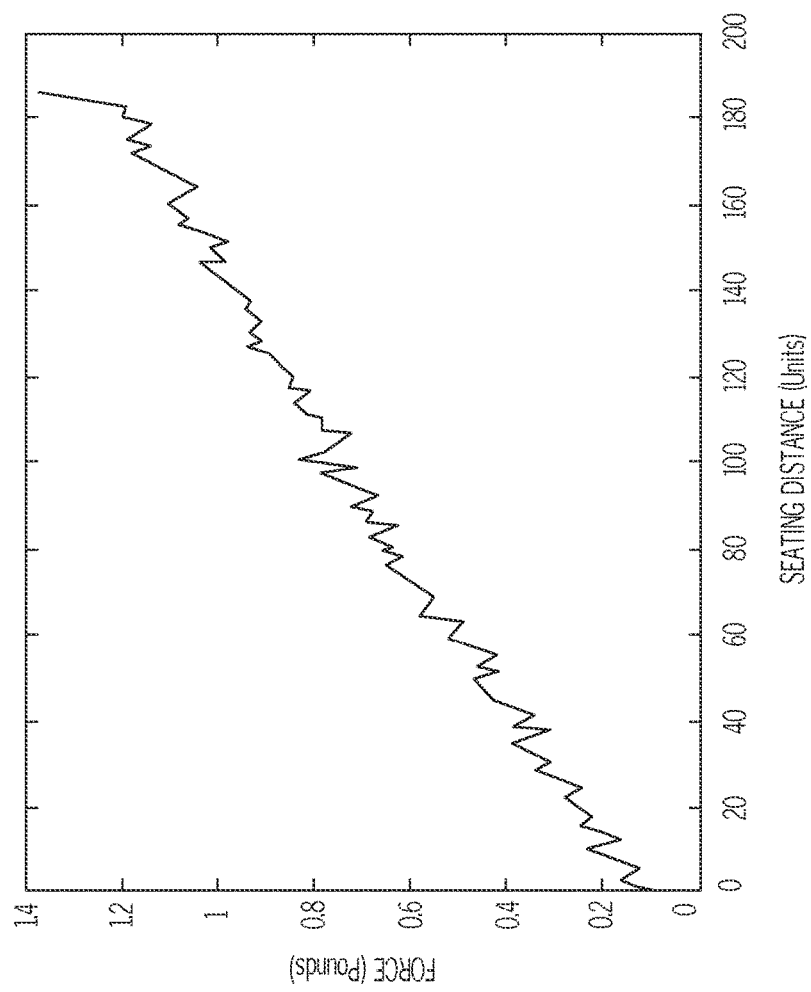
FIG. 6 is a plot of force versus slide actuator position (or an equivalent metric) during a reservoir seating action performed under a blocked vent condition.

If, however, the reservoir cavity vent 113 is blocked (e.g., the permeable membrane of the fitting 110 is wet), then force begins to rise shortly after the seating operation begins and increases continuously until it reaches the seating threshold. FIG. 6 is a plot of force versus slide actuator position (or drive motor count, travel distance, or any suitable metric) during a reservoir seating action performed under a blocked vent condition. As shown in FIG. 6, the force increases as the slide actuator 121 advances rather than holding steady for most of the duration of the seating operation. Eventually, the force reaches nearly 1.4 pounds. Notably, this force characteristic may falsely indicate a seated reservoir whether or not the slide actuator 121 has actually seated with the piston 144.

Figure 7:
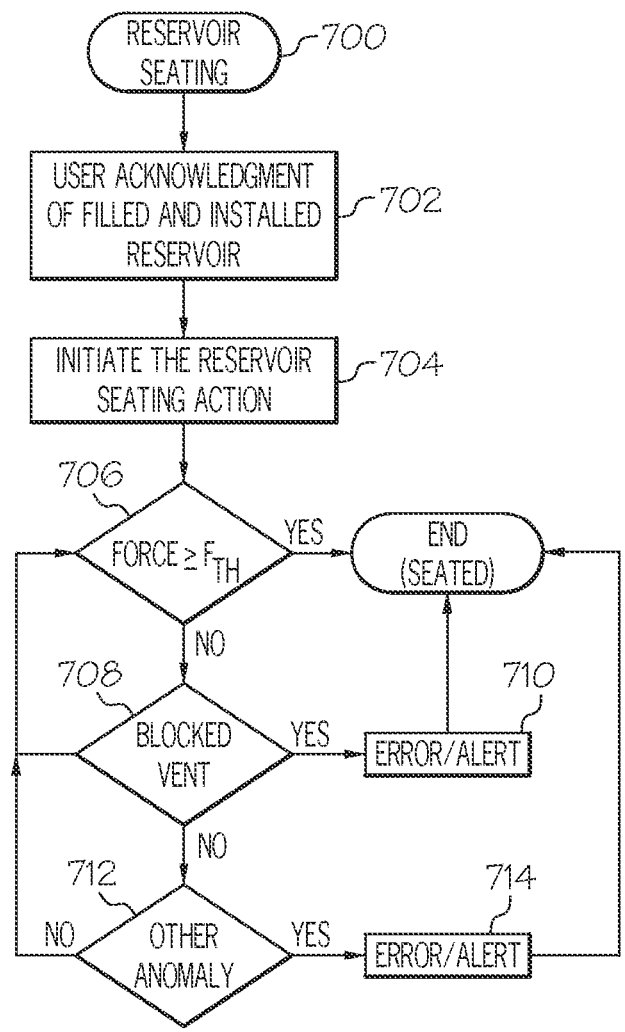
FIG. 7 is a flow chart that illustrates an exemplary embodiment of a reservoir seating process.

FIG. 7 is a flow chart that illustrates an exemplary embodiment of a reservoir seating process 700. An iteration of the process 700 may be performed whenever a fluid reservoir is inserted into the reservoir cavity of the fluid infusion device, to prepare the reservoir for delivery operations. To this end, the process 700 may begin in response to a user acknowledgment of a filled (or partially filled) and installed fluid reservoir (task 702). Task 702 may rely on a manual confirmation by the user, e.g., activation of a confirmation message, manipulation of a button on the device, or the like. After receiving and processing the user acknowledgment, the process 700 initiates the reservoir seating action (task 704), which is intended to seat the slide actuator 121 with the piston 144. During the reservoir seating action, the fluid infusion device is controlled to advance the slide actuator while obtaining force measurements corresponding to different slide actuator positions.

The process 700 obtains force measurements for a reservoir seating action of the drive motor assembly of the fluid infusion device. As explained above: the drive motor is controlled to rotate in a regulated manner; rotation of the drive motor results in rotation of the drive screw 125; rotation of the drive screw 125 advances the slide actuator 121 (forward toward the piston 144 of the fluid reservoir 111, or backward corresponding to a rewind movement); and forward movement of the slide actuator 121 is intended to seat the slide actuator 121 with the piston 144. The process 700 obtains force measurements that correspond to, are mapped to, are translated to, or are otherwise associated with the different positions of the slide actuator 121 during the seating action. In practice, each position of the slide actuator 121 may be represented by any suitable metric, measurement, quantity, and/or value that can be handled by the fluid infusion device. For example, embodiments of the fluid infusion device may keep track of motor steps (e.g., encoder counts) relative to a reference position such as the fully rewound position of the slide actuator 121. In such embodiments, the motor count at any given time during the seating operation provides an indication of the position of the slide actuator 121 relative to the fully rewound position. The motor count at any given time also provides an indication of the travel distance of the slide actuator 121 relative to the fully rewound position. Although certain preferred embodiments of the process 700 consider and analyze motor counts or motor steps, alternative embodiments may consider and handle any type of distance measurement, travel measurement, motor position measurement, and/or other metrics in an equivalent manner. These and other measurements and metrics that are associated with the force measurements are contemplated by the following description.

In accordance with conventional methodologies, the initiated reservoir seating action monitors the force measurements to determine whether a predetermined seating threshold force has been reached (query task 706). During the seating operation, if the measured force exceeds this seating threshold (the "Yes" branch of query task 706), the motor is stopped to inhibit further travel of the slide actuator, and the process 700 ends. In certain embodiments, the seating threshold is about 1.4 pounds. In alternative embodiments, higher or lower seating thresholds may be used depending on the force required to urge fluid from the fluid reservoir 111, the force required to overcome the back pressure of pushing fluids from the fluid reservoir 111 through the tubing 108, the speed of the motor 136, the accuracy and resolution of the force sensor 126, or the like.

If the measured force is less than the seating threshold value (the "No" branch of query task 706), then the process 700 checks for a blocked vent condition (query task 708) and for any other anomalies (query task 712). The process 700 analyzes the obtained force measurements and the corresponding distance/position measurements to determine whether the reservoir cavity vent is blocked. If the vent is deemed to be blocked (the "Yes" branch of query task 708), then the process 700 may initiate and execute appropriate corrective action (task 710). Similarly, if the process 700 detects another anomaly that requires attention, then corrective action can be taken (task 714). The corrective action taken by the fluid infusion device may include one or more of the following, without limitation: instructing or requiring the user to rewind the pump (i.e., move the slide actuator away from the direction of fluid delivery); generating an alert or an alarm at the fluid infusion device; stopping or inhibiting fluid delivery; presenting instructions, a maintenance reminder, or a message to the user; or the like. In practice, an alert, alarm, or warning may include, without limitation: sounds; one or more synthesized voices; vibrations or other haptic feedback; displayed symbols or messages; lights; transmitted signals; Braille output; or the like. Other forms of corrective action include, without limitation: running a self-test of the fluid infusion device; recalibrating the threshold forces; temporarily disabling the fluid infusion device; or the like. As depicted in FIG. 7, if corrective action is taken in this manner, the reservoir seating action is terminated and the slide actuator 121 is no longer advanced.

In accordance with certain embodiments, the characteristics of the force measurements are analyzed during the reservoir seating action to detect a blocked vent condition (see query task 706). A number of techniques and approaches are presented here, and any number of these techniques could be performed concurrently or in parallel during reservoir seating. One methodology detects excessive force slope during seating. As explained above, when the reservoir cavity 134 is not being vented properly, force increases as air becomes compressed inside the reservoir cavity 134 instead of venting through the membrane. The force increase is gradual and can be detected by monitoring the general trend of the force measurement signal. In accordance with one proposed solution, a variable-length measurement window of force is analyzed, across which the rate of increase can be determined Evaluation methods may include a difference in end-to-end magnitude, a linear fit across the window, or other methods of determining data trends. Once a slope value is computed, it is compared to a threshold; a fault signal is generated if that threshold is exceeded.

Figure 8:
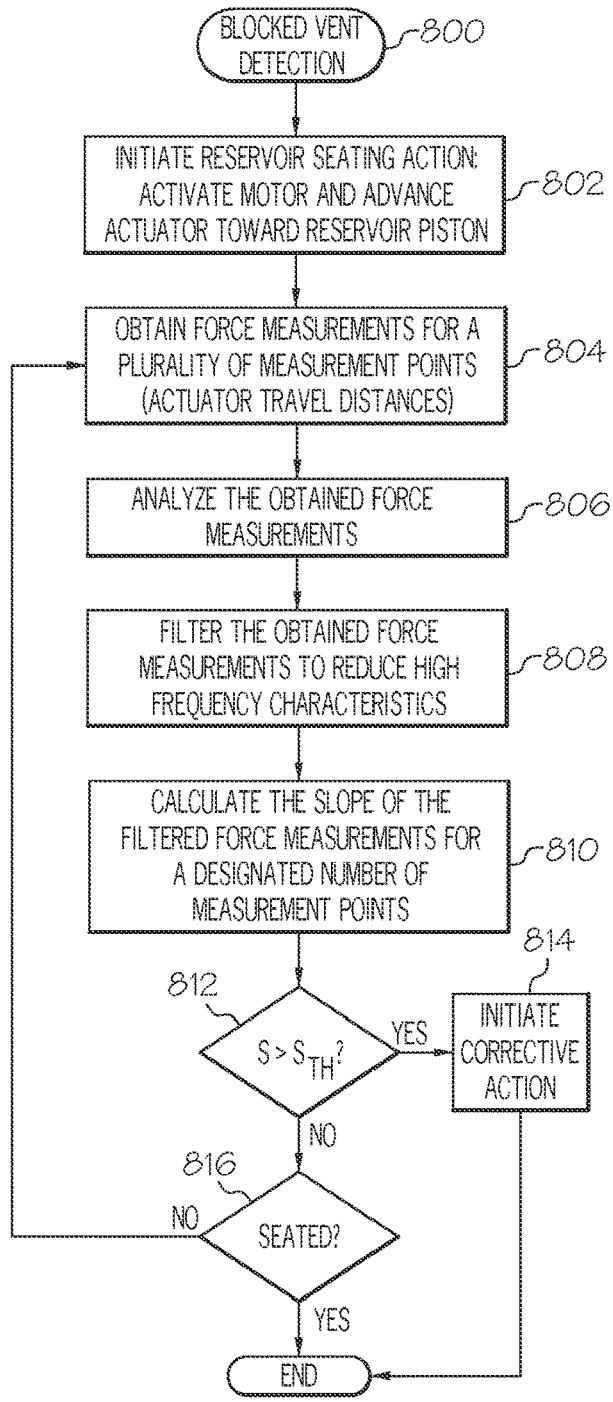
FIGS. 8-13 are flow charts that illustrate various exemplary embodiments of a blocked vent detection process.

FIG. 8 is a flow chart that illustrates an exemplary embodiment of a blocked vent detection process 800, which may be performed by the fluid infusion device in association with the reservoir seating process 700. Accordingly, the process 800 may initiate the reservoir seating action as described above. During reservoir seating, the fluid infusion device controls the activation of the motor to advance the slide actuator toward the reservoir piston (task 802). The process 800 obtains force measurements for a plurality of different measurement points during the seating operation (task 804). Each measurement point corresponds to a respective position of the slide actuator, a respective travel distance of the slide actuator, a motor encoder or step count, a motor position, or the like. Accordingly, task 804 may also obtain and record the distance, position, and/or count measurements that correspond to the obtained force measurements. As mentioned above, each force measurement indicates a measure of force imparted to the force sensor during the reservoir seating action, and each force measurement is associated with a corresponding travel distance measurement of the slide actuator.

The obtained force measurements can be analyzed and processed after the data for a sufficient number of measurement points has been collected (task 806). In this regard, it may be necessary or desirable for the process 800 to collect force measurements for a designated amount of slide actuator travel before determining whether the reservoir cavity vent is blocked. For example, the process 800 may continue gathering force measurements and related travel distance measurements for a period beginning at the fully rewound position of the slide actuator and ending after a predetermined number of motor steps or encoder counts. In certain embodiments, the force measurements are collected for about 50 counts, which corresponds to approximately 0.5 Units of delivered fluid. Of course, more or less than 50 counts could be utilized in other embodiments.

This description assumes that a sufficient number of measurement points have been sampled for purposes of further processing. In accordance with some embodiments, an optional signal filtering procedure is performed to condition the force measurement data (task 808). Even during normal operation, the obtained force measurement signal may exhibit a sinusoidal periodic feature. In order to prevent a slope threshold from being triggered by components of this feature (e.g., the slope between a valley and a peak of the force measurement data), it is desirable to remove it or reduce its amplitude. The force measurement signal may be filtered with an appropriate low-pass filter to preserve only the general trend. The high frequency characteristics could be detected during normal device operation, during prior known good seating procedures, or during manufacturing, wherein those characteristics can be subtracted from the measurement signal.

Accordingly, during task 808, the force measurement data is filtered using an appropriate signal filtering algorithm to reduce high frequency characteristics. Referring back to FIG. 6, a suitably designed signal filter can be applied to the raw force measurement data to reduce the saw tooth characteristics in the illustrated force-versus-distance plot. Thereafter, the filtered force measurements can be analyzed and processed in the manner described below.

The filtered or unfiltered force measurements are analyzed to determine whether the vent in the reservoir cavity is blocked. For this example, the process 800 calculates a slope (rate of change) of force-versus-distance for the filtered force measurements, over a designated number of measurement points (task 810). The force slope may be calculated using any suitable formula, algorithm, technique, or methodology. This particular example calculates the slope based on the two "endpoints" of the analysis window. The simple linear slope calculation employed by the process 800 disregards measurement points taken between the two endpoints. Alternate embodiments may, of course, consider any number of intervening measurement points if so desired.

The calculated slope (S) is compared to a threshold slope value ($S_{TH}$) to determine whether the vent is blocked (query task 812). In this regard, the process 800 determines that the vent is blocked when the calculated slope is greater than the threshold slope value, and otherwise determines that the vent is not blocked. Referring again to FIG. 5, the force slope will usually be very low (i.e., close to zero) for the duration of the seating operation. Thus, the threshold slope value may be chosen to be any nonzero value, with the actual value being selected according to the desired sensitivity. As one non-limiting example, the threshold slope value may be within the range of about 0.25 to about 1.0 pounds per unit of distance.

If the calculated slope exceeds the threshold slope value (the "Yes" branch of query task 812), then the process 800 initiates corrective action for the fluid infusion device (task 814). As explained above with reference to the process 700, the corrective action may include the generation of an error message, a user alert, or the like. Moreover, the corrective action may terminate the seating action and stop the motor such that the slide actuator no longer advances toward the piston.

If the calculated slope does not exceed the threshold slope value (the "No" branch of query task 812), then the process 800 may continue by checking whether proper seating has been achieved (query task 816). If the slide actuator is seated with the piston (the "Yes" branch of query task 816), then the process 800 ends. If the slide actuator has not yet reached the piston (the "No" branch of query task 816), then the process 800 may exit or return to task 804 to continue as described above. The next iteration of the process 800 may be performed after the next force measurement has been obtained, after a designated number of new force measurements have been obtained, etc. Moreover, the next slope calculation may be based on a moving window of measurement points, or it may be based on a larger window that contemplates any newly obtained force measurements.

Figure 9:
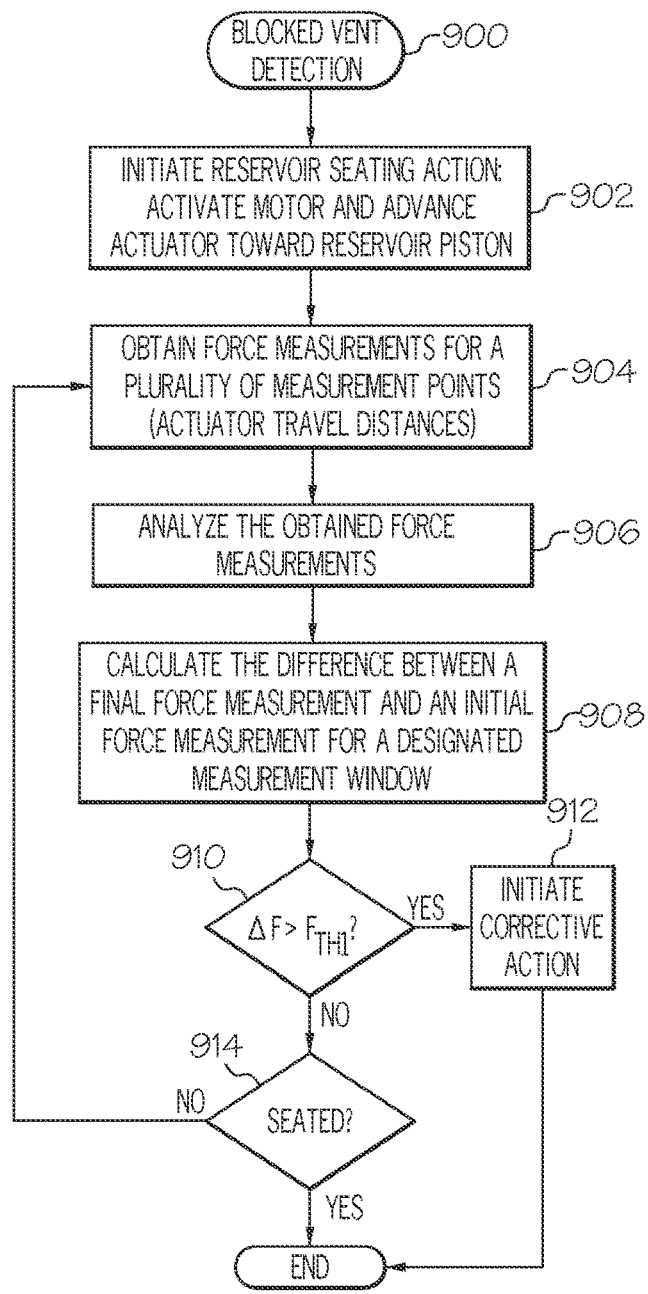

The process 800 represents one methodology for detecting a blocked reservoir cavity vent during a reservoir seating operation. FIG. 9 is a flow chart that illustrates a similar blocked vent detection process 900 that instead relies on the difference between two measured force values. For the sake of brevity and clarity, features and tasks that are common between the process 800 and the process 900 will not be redundantly described below with reference to FIG. 9.

The process 900 initiates the reservoir seating action (task 902), obtains force and travel distance measurements (task 904), and analyzes the obtained force measurements (task 906), which may be filtered or unfiltered, as described above. The process 900 may continue by calculating a difference between a second or final force measurement and a first or initial force measurement (task 908). The two force measurements may correspond to the endpoints of a designated measurement window, or they may correspond to any two measurement points that fall within a measurement window. The calculated difference ($\Delta F$) is compared to a threshold force value ($F_{TH1}$) that is chosen as an indicator of a blocked vent (query task 910). Thus, the threshold force value may be chosen to be any nonzero value, with the actual value being selected according to the desired sensitivity and/or according to the length of the measurement window between the two force measurements used to calculate the difference. As one non-limiting example, the threshold force value may be within the range of about 0.5 to about 1.0 pounds.

If the calculated force difference exceeds the threshold force value (the "Yes" branch of query task 910), then the process 900 initiates corrective action (task 912) and terminates the seating operation. If the calculated force difference does not exceed the threshold force value (the "No" branch of query task 910), then the process 900 may check for proper seating (query task 914) and proceed in the manner described above for the process 800. Subsequent iterations of the process 900 may be performed after the next force measurement has been obtained, after a designated number of new force measurements have been obtained, etc. Moreover, the next difference calculation may be based on the most recent force measurement endpoints, or any two force measurements within the current measurement window.

Certain embodiments of the fluid infusion device may also employ an early trigger mechanism in conjunction with the process 800 and/or in conjunction with the process 900. In this regard, although the detection of slope trends may commence only after sufficient data is available to fill the evaluation window, it is also desirable to detect improper venting as early in the seating procedure as possible. In some instances, the magnitude of force at or near the beginning of the seating operation may be used to detect abnormal force characteristics. The magnitude of force in a normal seating procedure is relatively low, such that a low threshold may be used to detect if there is an early indication that the force is higher than normal.

In accordance with this early trigger approach, the fluid infusion device may compare an initial force measurement (obtained early in the reservoir seating operation) to an early detection threshold force value. If the initial force measurement is greater than the early detection threshold force value, then the device can immediately initiate the process 800 and/or the process 900, generate an alert, and/or initiate any or all of the other processes described in more detail below. The initial force trigger may also serve as a condition that must be satisfied before the process 800 or the process 900 can be fully performed. For example, analyzing the obtained force measurements (in the manner described above) need not be performed unless the initial force measurement exceeds the designated early detection threshold force value.

Certain embodiments of the fluid infusion device may also consider the reservoir fill level when determining whether the reservoir cavity vent is blocked. More specifically, the device may include an option for the user to enter an approximate reservoir fill amount, volume, or level. The device can then estimate the travel distance required to achieve seating with the piston, based on the user-entered fill amount. As explained above, the slide actuator is fully rewound prior to the start of the seating operation. Thus, if the approximate amount of driving distance required to seat the reservoir is known, a significant force observed during this driving distance would likely be caused from air being compressed by the travel of the slide actuator. The device can signal a fault in this case, which can reduce the detection time because it would not be necessary to wait for the nominal slope detection window to be filled with measurement points.

Figure 10:
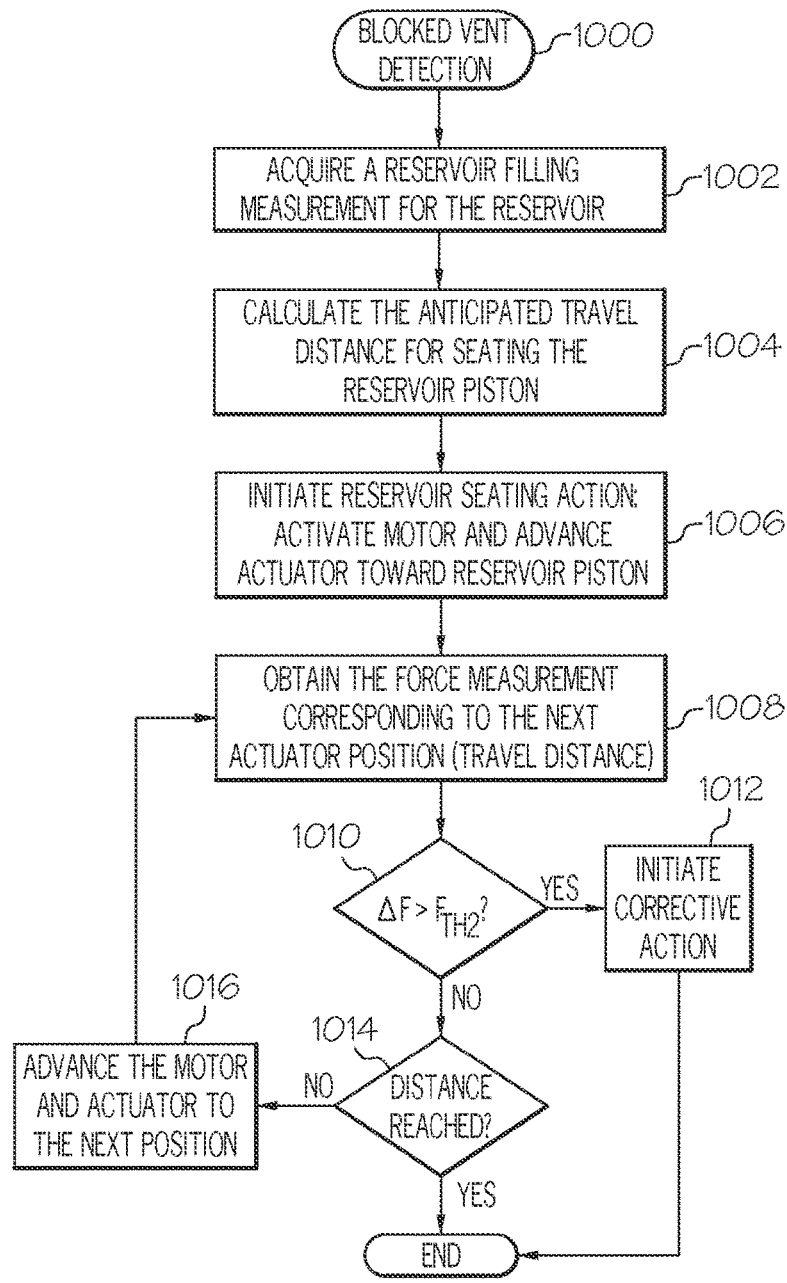

FIG. 10 is a flow chart that illustrates another exemplary embodiment of a blocked vent detection process 1000 that leverages a reservoir filling measurement. The process 1000 could be executed in parallel with one or more of the other processes described herein. In alternative embodiments, the process 1000 could be performed by itself. For the illustrated embodiment, the process 1000 acquires a reservoir filling measurement for the fluid reservoir that is installed in the reservoir cavity (task 1002). In practice, the reservoir filling measurement may be entered by the user or patient, and the value may be expressed in Units of medication fluid. In this regard, the process 1000 assumes that the user has accurately recorded, entered, or otherwise noted the amount of fluid that was introduced into the fluid reservoir prior to installation.

Next, the process 1000 calculates an anticipated travel distance (of the slide actuator) for seating the piston of the reservoir (task 1004). The calculated distance is based on, or is otherwise influenced by, the user-entered filling measurement. Thus, task 1004 relies on known relationships between fill volume, piston location, and slide actuator travel distance. For example, if the fluid reservoir is completely filled, then the piston will be positioned at or near the bottom end of the reservoir (see FIG. 3 for reference), and the seating travel distance for the slide actuator will be relatively short. In contrast, if the fluid reservoir is only half filled, then the piston will be positioned near the middle of the reservoir barrel, and the corresponding seating travel distance will be relatively long.

The process 1000 initiates the reservoir seating action, and activates the motor to advance the slide actuator (task 1006). During the reservoir seating action, the process 1000 obtains force measurements corresponding to different slide actuator positions, which represent different actuator travel distances (task 1008). For each measurement point, the process 1000 compares the force measurement to an early detection threshold force value ($F_{TH2}$) that is chosen as an indicator of a blocked vent (query task 1010). Thus, the value of $F_{TH2}$ may be chosen to be any nonzero value, with the actual value being selected according to the desired sensitivity and/or according to the calculated anticipated travel distance. As one non-limiting example, the threshold force value may be within the range of about 1.0 to about 1.4 pounds.

If the force measurement is greater than the early detection threshold force value (the "Yes" branch of query task 1010), then the process 1000 initiates corrective action (task 1012) and terminates the seating operation. If the force measurement does not exceed the early detection threshold force value (the "No" branch of query task 1010), then the process 1000 checks whether the calculated anticipated travel distance has been reached (query task 1014). If so, then the process 1000 ends. If the anticipated travel distance has not been reached (the "No" branch of query task 1014), then the process 1000 returns to task 1008 to obtain the next force measurement and proceeds as described above.

Some embodiments of the fluid infusion device may also consider an end-of-seating force increase rate when determining whether the reservoir cavity vent is blocked. It is desirable for the device to be able to detect improper venting before the seating force threshold is actually reached. However, if it is unable to do so, it may still be useful to detect a blocked vent immediately after seating to alert the system or the user of an issue. A solution presented here utilizes the fact that, during normal seating, the force rises very rapidly when it reaches fluid and crosses the seating threshold quickly. If an intermediate threshold is set slightly below the seating force threshold, the device can determine the time it took for the force to rise from the intermediate threshold to the final threshold, and signal a fault if the determined time is too long. For example, if the seating threshold is 1.4 pounds, the intermediate threshold may be chosen to be 1.0 pound, with an expectation that the time between a force measurement of 1.0 pound and a subsequent force measurement of 1.4 pounds should be very short.

Figure 11:
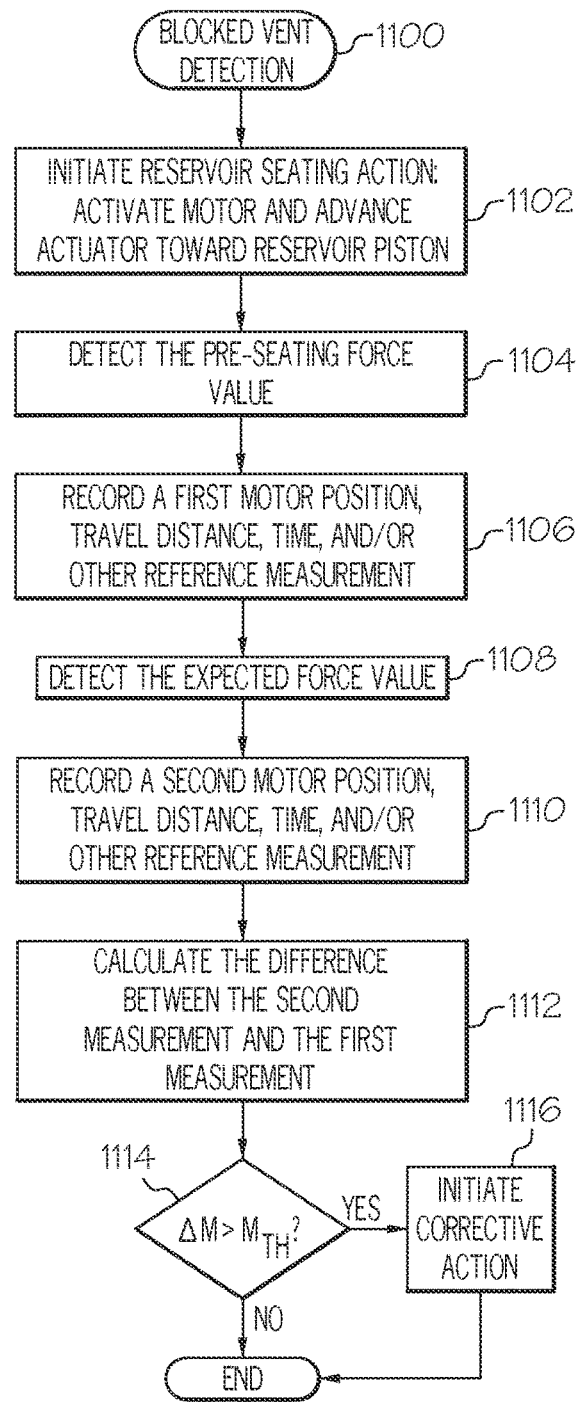

FIG. 11 is a flow chart that illustrates another exemplary embodiment of a blocked vent detection process 1100 that considers an end-of-seating period. The process 1100 could be executed in parallel with one or more of the other processes described herein. In alternative embodiments, the process 1100 could be performed by itself. For the illustrated embodiment, the process 1100 initiates the reservoir seating action, activates the drive motor, and advances the slide actuator toward the reservoir piston (task 1102). During the seating operation, the process 1100 detects when a force measurement reaches a pre-seating force value (task 1104). In accordance with the non-limiting example described here, the pre-seating force value is 1.0 pound. The process 1100 records a measurement that corresponds to the detected pre-seating force value (task 1106). Depending on the particular embodiment, the recorded measurement may represent a motor position, a motor step count, an encoder count, a slide actuator travel distance, a time, a slide actuator position, and/or some other type of reference measurement. This example assumes that task 1106 records a first distance measurement that corresponds to the detection of the pre-seating force value.

Thereafter, the process 1100 detects when a force measurement reaches an expected seating force value (task 1108). In accordance with the non-limiting example described here, the expected seating force value is 1.4 pounds. The process 1100 records another measurement that corresponds to the detected seating force value (task 1110). Depending on the particular embodiment, the recorded measurement may represent a motor position, a motor step count, an encoder count, a slide actuator travel distance, a time, a slide actuator position, and/or some other type of reference measurement. This example assumes that task 1110 records a second distance measurement that corresponds to the detection of the expected seating force value.

The process 1100 may continue by calculating a difference between the second distance measurement and the first distance measurement (task 1112). The calculated difference ($\Delta M$) is compared to a threshold seating distance ($M_{TH}$) that is chosen as an indicator of a blocked vent (query task 1114). Under normal conditions, the threshold seating distance will be very short because the measured force quickly rises to the expected seating force (see FIG. 5). As one non-limiting example, the threshold seating distance may be within the range of about 0.5 to about 1.5, expressed in U-100 insulin units.

If the calculated difference ($\Delta M$) is greater than the threshold seating distance (the "Yes" branch of query task 1114), then the process 1100 initiates corrective action (task 1116) and terminates the seating operation. Otherwise, the process 1100 may end, under the assumption that the seating operation has been properly executed.

The fluid infusion device could also utilize other slide actuator drive profiles in an attempt to detect a blocked reservoir cavity vent and/or in an attempt to mitigate the consequences of a blocked reservoir cavity vent. As mentioned above, the slide actuator is driven forward in a continuous manner during a seating operation. In accordance with one proposed methodology, the slide actuator is paused for short periods of time during the forward drive. Pausing in this manner allows the fluid infusion device to measure force while the slide actuator and motor are stationary. Under normal conditions, the measured force should be relatively low at times when the slide actuator is not moving forward. Thus, the presence of a significant force (when the slide actuator is stationary) can indicate pressure within the reservoir cavity, wherein such pressure could be indicative of a blocked vent.

In accordance with another proposed methodology, the slide actuator is driven backwards for a short distance before being driven forward again. If the reservoir cavity is vented properly, the measured force should not change by a significant amount. If, however, the reservoir cavity it is not being vented properly, the measured force may decrease when the slide actuator is rewound (because the pressure of the trapped air remaining in the reservoir cavity decreases in response to the larger cavity volume). Consequently, this type of decrease in the measured force can help to detect improper venting.

Figure 12:
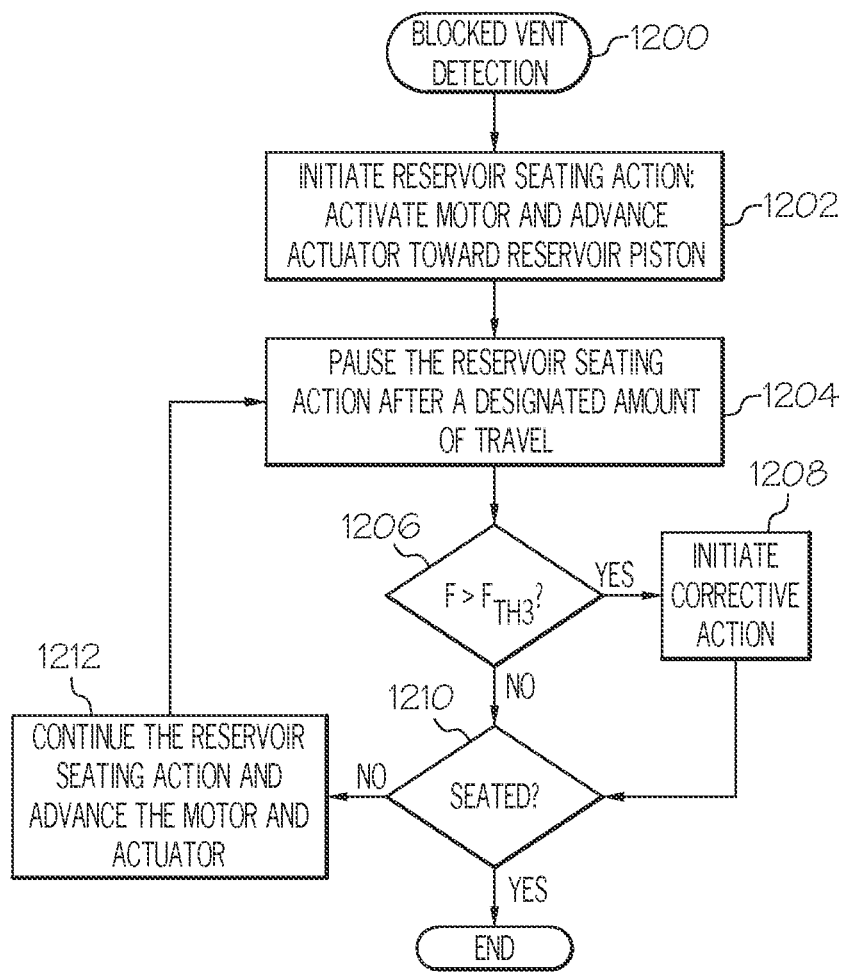

FIG. 12 is a flow chart that illustrates an exemplary embodiment of a blocked vent detection process 1200 that checks force measurements while the slide actuator is stationary during a reservoir seating operation. The process 1200 could be executed in parallel with one or more of the other processes described herein. In alternative embodiments, the process 1200 could be performed by itself. For the illustrated embodiment, the process 1200 initiates the reservoir seating action, activates the drive motor, and advances the slide actuator toward the reservoir piston (task 1202). The process 1200 pauses the reservoir seating action (task 1204) to place the drive motor and the slide actuator into a stationary state. The pausing performed during task 1204 may occur after a designated amount of actuator travel, after a designated number of motor steps or encoder counts, after a designated amount of time, or the like.

The force measurement obtained during the pause is compared to a threshold force value ($F_{TH3}$) that is chosen as an indicator of a blocked vent (query task 1206). Thus, the value of $F_{TH3}$ may be chosen to be any nonzero value. As one non-limiting example, the value of $F_{TH3}$ may be within the range of about 0.0 to about 0.3 pounds.

If the force measurement obtained during the pause is greater than $F_{TH3}$ (the "Yes" branch of query task 1206), then the process 1200 initiates corrective action (task 1208) and terminates the seating operation. If the force measurement does not exceed $F_{TH3}$ (the "No" branch of query task 1206), then the process 1200 may check for proper seating (query task 1210). If query task 1210 determines that the reservoir is properly seated, then the process 1200 ends.

If, however, the process 1200 determines that the reservoir is not yet seated (the "No" branch of query task 1210), then the reservoir seating action continues (task 1212). In this regard, the motor and the slide actuator are activated again such that the slide actuator is advanced forward by the desired amount. Thereafter, the process 1200 may return to task 1204 (pausing the slide actuator once again) and proceed in the manner described above.

Figure 13:
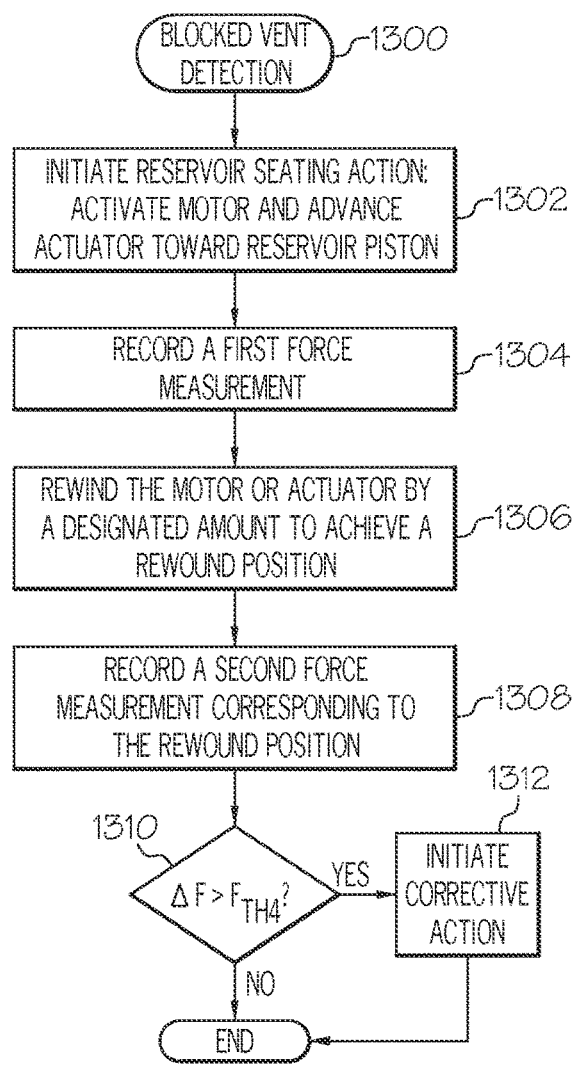

FIG. 13 is a flow chart that illustrates an exemplary embodiment of a blocked vent detection process 1300 that rewinds the slide actuator during a reservoir seating operation. The process 1300 could be executed in parallel with one or more of the other processes described herein. In alternative embodiments, the process 1300 could be performed by itself. For the illustrated embodiment, the process 1300 initiates the reservoir seating action, activates the drive motor, and advances the slide actuator toward the reservoir piston (task 1302). The process 1300 records a first force measurement during the reservoir seating action (task 1304), e.g., a force measurement corresponding to a first reference measurement point. After recording the first force measurement, the process 1300 rewinds the drive motor assembly by a designated amount to achieve a rewound position (task 1306). The rewind amount may vary from one embodiment to another, and from one seating operation to another. In accordance with certain non-limiting embodiments, task 1306 rewinds the slide actuator by about five to about fifty motor counts. The process 1300 also records a second force measurement that corresponds to the rewound position (task 1308).

The process 1300 may continue by calculating a difference between the second force measurement and the first force measurement to obtain a force difference. This force difference ($\Delta F$) is compared to a threshold force value ($F_{TH4}$) that is chosen as an indicator of a blocked vent (query task 1310). For example, if the second force measurement (taken at the rewound position) is less than the first force measurement by a predetermined amount, then the process assumes that the reservoir cavity vent is blocked. Accordingly, if the calculated force difference is greater than $F_{TH4}$ (the "Yes" branch of query task 1310), then the process 1300 initiates corrective action (task 1312) and terminates the seating operation. If the calculated force difference does not exceed $F_{TH4}$ (the "No" branch of query task 1310), then the process 1300 may exit or it may be repeated with another set of recorded force measurements (a forward force value and a rewound force value).

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of operating a fluid infusion device comprising a drive motor assembly, a force sensor associated with the drive motor assembly, a reservoir cavity that accommodates a fluid reservoir having a piston, and an actuator coupled to the drive motor assembly to actuate the piston, the method comprising:
   obtaining a plurality of force measurements during a reservoir seating action of the drive motor assembly, the plurality of force measurements indicating measures of force imparted to the force sensor during the reservoir seating action;
   comparing an initial force measurement from the plurality of force measurements to an early detection threshold force value;
   initiating an analysis of additional force measurements from the plurality of force measurements only when the initial force measurement is greater than the early detection threshold force value;
   determining that a vent for equalizing air pressure inside the reservoir cavity is blocked and preventing air in the reservoir cavity from venting externally, based on the analysis of the additional force measurements, wherein the determining occurs before actual seating of the actuator in contact with the piston; and
   initiating corrective action for the fluid infusion device in response to determining that the vent in the reservoir cavity is blocked.

2. The method of claim 1, wherein initiating corrective action comprises terminating the reservoir seating action.

3. The method of claim 1, wherein initiating corrective action comprises generating a user alert at the fluid infusion device.

4. The method of claim 1, further comprising:
   obtaining a plurality of distance measurements during the reservoir seating action;
   calculating a slope of force-versus-distance for the plurality of distance measurements; and
   comparing the calculated slope of force-versus-distance to a threshold slope value, wherein the method determines that the vent in the reservoir cavity is blocked when the calculated slope is greater than the threshold slope value.

5. The method of claim 1, wherein:
   obtaining the plurality of force measurements comprises obtaining a first force measurement corresponding to a first distance measurement associated with the drive motor assembly, and obtaining a second force measurement corresponding to a second distance measurement associated with the drive motor assembly; and
   the method further comprises calculating a difference between the second force measurement and the first force measurement, wherein the method determines that the vent in the reservoir cavity is blocked when the calculated difference is greater than a threshold force value.

6. The method of claim 1, further comprising:
   filtering the obtained plurality of force measurements to reduce high frequency characteristics, wherein the determining is based on an analysis of the filtered force measurements.

7. The method of claim 1, further comprising:
   acquiring a reservoir filling measurement for the fluid reservoir;
   calculating an anticipated travel distance for seating the piston of the fluid reservoir, based on the acquired reservoir filling measurement;
   ascertaining, before the anticipated travel distance is reached, that the initial force measurement is greater than the early detection threshold force value; and
   generating an alert in response to the ascertaining.

8. The method of claim 1, further comprising:
   detecting a pre-seating force value during the reservoir seating action;
   recording a first distance measurement corresponding to the detected pre-seating force value;
   thereafter, detecting an expected seating force value during the reservoir seating action;
   recording a second distance measurement corresponding to the detected expected seating force value;
   calculating a difference between the second distance measurement and the first distance measurement; and
   generating an alert when the difference is greater than a threshold seating distance.

9. The method of claim 1, further comprising:
   pausing the reservoir seating action;
   obtaining the initial force measurement while the reservoir seating action is paused; and
   generating an alert when the initial force measurement is greater than the early detection threshold force value.

10. The method of claim 1, further comprising:
    recording a first force measurement during the reservoir seating action;
    after recording the first force measurement, rewinding the drive motor assembly to achieve a rewound position;
    recording a second force measurement while the drive motor assembly is in the rewound position; and
    generating an alert when the second force measurement is less than the first force measurement by at least a threshold amount.

11. A method of operating a fluid infusion device comprising a drive motor assembly, an actuator coupled to the drive motor assembly, and a reservoir that accommodates a fluid reservoir having a piston, the method comprising:
  initiating a reservoir seating action intended to seat the actuator with the piston of the fluid reservoir;
  obtaining, for each of a plurality of travel distance measurement points associated with the reservoir seating action, a respective force measurement that is indicative of air pressure inside the reservoir cavity, resulting in a plurality of obtained force measurements;
  comparing an initial force measurement from the plurality of obtained force measurements to an early detection threshold force value;
  initiating processing of additional force measurements from the plurality of obtained force measurements and for at least two of the plurality of travel distance measurement points only when the initial force measurement is greater than the early detection threshold force value;
  determining that a vent for equalizing air pressure inside the reservoir cavity is blocked and preventing air in the reservoir cavity from venting externally, based on the processing of the additional force measurements, wherein the determining occurs before actual seating of the actuator in contact with the piston; and
  initiating corrective action for the fluid infusion device in response to determining that the vent in the reservoir cavity is blocked.

12. The method of claim 11, wherein initiating corrective action comprises generating an alert at the fluid infusion device.

13. The method of claim 11, wherein the processing comprises:
  calculating a slope of force-versus-distance for the additional force measurements; and
  comparing the calculated slope of force-versus-distance to a threshold slope value, wherein the method determines that the vent in the reservoir cavity is blocked when the calculated slope is greater than the threshold slope value.

14. The method of claim 11, wherein the processing comprises:
  calculating a difference between a first force measurement and a second force measurement, wherein the method determines that the vent in the reservoir cavity is blocked when the calculated difference is greater than a threshold force value.

15. The method of claim 11, further comprising:
  filtering the plurality of obtained force measurements to reduce high frequency characteristics, wherein the processing is performed on filtered force measurements.

16. The method of claim 11, further comprising:
  acquiring a reservoir filling measurement for the fluid reservoir;
  calculating an anticipated travel distance for seating the actuator with the piston of the fluid reservoir, based on the acquired reservoir filling measurement;
  ascertaining, before the anticipated travel distance is reached, that the initial force measurement is greater than the early detection threshold force value; and
  generating an alert in response to the ascertaining.

17. The method of claim 11, further comprising:
  detecting a pre-seating force value during the reservoir seating action;
  recording a first distance measurement corresponding to the detected pre-seating force value;
  thereafter, detecting an expected seating force value during the reservoir seating action;
  recording a second distance measurement corresponding to the detected expected seating force value;
  calculating a difference between the second distance measurement and the first distance measurement; and
  generating an alert when the difference is greater than a threshold seating distance.

18. The method of claim 11, further comprising:
  pausing the reservoir seating action;
  obtaining the initial force measurement while the reservoir seating action is paused; and
  generating an alert when the initial force measurement is greater than the early detection threshold force value.

19. The method of claim 11, further comprising:
  recording a first force measurement during the reservoir seating action;
  after recording the first force measurement, rewinding the actuator to achieve a rewound position;
  recording a second force measurement while the actuator is in the rewound position; and
  generating an alert when the second force measurement is less than the first force measurement by at least a threshold amount.

20. A device for delivering fluid to a user, the device comprising:
  a housing;
  a reservoir cavity within the housing to accommodate fluid reservoirs;
  a drive motor assembly in the housing to advance an actuator for a piston of a fluid reservoir;
  a force sensor associated with the drive motor assembly to generate output levels in response to force imparted thereto, the output levels corresponding to force measurements; and
  an electronics module coupled to the force sensor to process the output levels during a reservoir seating action intended to seat the actuator with the piston of the fluid reservoir by:
    obtaining a plurality of force measurements from the force sensor during the reservoir seating action, the plurality of force measurements indicating measures of force imparted to the force sensor during the reservoir seating action;
    comparing an initial force measurement from the plurality of force measurements to an early detection threshold force value;
    initiating an analysis of additional force measurements from the plurality of force measurements only when the initial force measurement is greater than the early detection threshold force value;
    determining that a vent for equalizing air pressure inside the reservoir cavity is blocked and preventing air in the reservoir cavity from venting externally, based on the analysis of the additional force measurements, wherein the determining occurs before actual seating of the actuator in contact with the piston; and
    initiating corrective action for the fluid infusion device in response to determining that the vent in the reservoir cavity is blocked.

21. The device of claim 20, wherein the electronics module initiates the corrective action by generating a user alert.

22. The device of claim 20, wherein, during the reservoir seating action, the electronics module:
  obtains a plurality of distance measurements;

calculates a slope of force-versus-distance for the plurality of distance measurements; and compares the calculated slope of force-versus-distance to a threshold slope value, wherein the electronics module determines that the vent in the reservoir cavity is blocked when the calculated slope is greater than the threshold slope value.

23. The device of claim 20, wherein, during the reservoir seating action, the electronics module:

obtains a first force measurement corresponding to a first distance measurement associated with the drive motor assembly;

obtains a second force measurement corresponding to a second distance measurement associated with the drive motor assembly; and calculates a difference between the second force measurement and the first force measurement, wherein the electronics module determines that the vent in the reservoir cavity is blocked when the calculated difference is greater than a threshold force value.

24. The device of claim 20, wherein:

the electronics module filters the obtained plurality of force measurements to reduce high frequency characteristics; and the determination made by the electronics module is based on an analysis of the filtered force measurements.

* * * * *